United States Patent
Andreas et al.

(10) Patent No.: US 8,460,358 B2
(45) Date of Patent: Jun. 11, 2013

(54) RAPID EXCHANGE INTERVENTIONAL DEVICES AND METHODS

(75) Inventors: Bernard Andreas, Redwood City, CA (US); Jeffry J. Grainger, Portola Valley, CA (US)

(73) Assignee: J.W. Medical Systems, Ltd., Weihai Shandong (CN)

( * ) Notice: Subject to any disclaimer, the term of this patent is extended or adjusted under 35 U.S.C. 154(b) by 638 days.

(21) Appl. No.: 11/952,644

(22) Filed: Dec. 7, 2007

(65) Prior Publication Data
US 2008/0097299 A1    Apr. 24, 2008

Related U.S. Application Data

(62) Division of application No. 10/814,581, filed on Mar. 30, 2004, now Pat. No. 7,323,006.

(51) Int. Cl.
*A61F 2/06* (2006.01)
(52) U.S. Cl.
USPC ........................................................ 623/1.11
(58) Field of Classification Search
USPC ..... 604/103.04, 171, 174; 606/194; 623/1.11, 623/1.12, 2.11
See application file for complete search history.

(56) References Cited

U.S. PATENT DOCUMENTS

| | | |
|---|---|---|
| 4,069,825 A | 1/1978 | Akiyama |
| 4,468,224 A | 8/1984 | Enzmann et al. |
| 4,512,338 A | 4/1985 | Balko |
| 4,564,014 A | 1/1986 | Fogarty et al. |
| 4,580,568 A | 4/1986 | Gianturco |
| 4,681,110 A | 7/1987 | Wiktor |
| 4,690,684 A | 9/1987 | McGreevy et al. |
| 4,733,665 A | 3/1988 | Palmaz |
| 4,739,762 A | 4/1988 | Palmaz |
| 4,748,982 A | 6/1988 | Horzewski et al. |
| 4,762,129 A | 8/1988 | Bonzel |
| 4,770,176 A | 9/1988 | McGreevy et al. |
| 4,775,337 A | 10/1988 | Van Wagener et al. |
| 4,776,337 A | 10/1988 | Palmaz |

(Continued)

FOREIGN PATENT DOCUMENTS

| | | |
|---|---|---|
| DE | 1 953 1659 | 3/1997 |
| DE | 1 963 0469 | 1/1998 |

(Continued)

OTHER PUBLICATIONS

Colombo, "The Invatec Bifurcation Stent Solution" Bifurcation Stents: Novel Solutions, TCT 2003, Washington: Sep. 15-19, 2003, 24 pages total.

(Continued)

*Primary Examiner* — Thomas McEvoy
(74) *Attorney, Agent, or Firm* — Kilpatrick Townsend & Stockton LLP

(57) ABSTRACT

Wire-guided interventional devices and methods are provided which enable faster and easier catheter exchanges. The interventional devices include a catheter shaft and a guidewire tube wherein the catheter shaft and the guidewire tube each have a length sufficient to extend to the vascular penetration when the interventional device is positioned at the treatment site. In some embodiments, a collar is disposed around the catheter shaft and guidewire tube that automatically inserts or removes the guidewire from the guidewire tube or automatically collapses or extends the guidewire tube as the catheter is introduced or withdrawn.

13 Claims, 8 Drawing Sheets

U.S. PATENT DOCUMENTS

| | | | |
|---|---|---|---|
| 4,886,062 A | 12/1989 | Wiktor | |
| 4,891,225 A | 1/1990 | Langer et al. | |
| 4,988,356 A | 1/1991 | Crittenden et al. | |
| 4,994,066 A | 2/1991 | Voss | |
| 4,994,069 A | 2/1991 | Ritchart et al. | |
| 4,994,298 A | 2/1991 | Yasuda | |
| 5,013,318 A | 5/1991 | Spranza, III | |
| 5,035,706 A | 7/1991 | Giantureo et al. | |
| 5,040,548 A | 8/1991 | Yock | |
| 5,061,273 A | 10/1991 | Yock | |
| 5,064,435 A | 11/1991 | Porter | |
| 5,092,877 A | 3/1992 | Pinchuk | |
| 5,102,417 A | 4/1992 | Palmaz | |
| 5,104,404 A | 4/1992 | Wolff | |
| 5,122,154 A | 6/1992 | Rhodes | |
| 5,135,535 A | 8/1992 | Kramer | |
| 5,158,548 A | 10/1992 | Lau et al. | |
| 5,192,297 A | 3/1993 | Hull | |
| 5,195,984 A | 3/1993 | Schatz | |
| 5,201,757 A | 4/1993 | Heyn et al. | |
| 5,217,495 A | 6/1993 | Kaplan et al. | |
| 5,219,355 A | 6/1993 | Parodi et al. | |
| 5,226,913 A | 7/1993 | Pinchuk | |
| 5,246,421 A | 9/1993 | Saab | |
| 5,261,887 A * | 11/1993 | Walker | 604/161 |
| 5,273,536 A | 12/1993 | Savas | |
| 5,282,824 A | 2/1994 | Gianturco | |
| 5,300,085 A | 4/1994 | Yock | |
| 5,312,415 A | 5/1994 | Palermo | |
| 5,328,469 A | 7/1994 | Coletti | |
| 5,334,187 A | 8/1994 | Fischell et al. | |
| 5,391,172 A | 2/1995 | Williams et al. | |
| 5,421,955 A | 6/1995 | Lau et al. | |
| 5,443,498 A | 8/1995 | Fontaine | |
| 5,445,646 A | 8/1995 | Euteneuer et al. | |
| 5,456,713 A | 10/1995 | Chuter | |
| 5,458,615 A | 10/1995 | Klemm et al. | |
| 5,470,315 A | 11/1995 | Adams | |
| 5,478,349 A | 12/1995 | Nicholas | |
| 5,484,444 A | 1/1996 | Braunschweiler et al. | |
| 5,490,837 A | 2/1996 | Blaeser et al. | |
| 5,496,346 A | 3/1996 | Horzewski et al. | |
| 5,501,227 A | 3/1996 | Yock | |
| 5,507,768 A | 4/1996 | Lau et al. | |
| 5,507,771 A | 4/1996 | Gianturco | |
| 5,514,093 A | 5/1996 | Ellis et al. | |
| 5,514,154 A | 5/1996 | Lau et al. | |
| 5,522,882 A | 6/1996 | Gaterud et al. | |
| 5,527,354 A | 6/1996 | Fontaine et al. | |
| 5,531,735 A | 7/1996 | Thompson | |
| 5,533,968 A * | 7/1996 | Muni et al. | 604/103.11 |
| 5,534,007 A | 7/1996 | St. Germain et al. | |
| 5,545,209 A | 8/1996 | Roberts et al. | |
| 5,549,551 A | 8/1996 | Peacock, III et al. | |
| 5,549,563 A | 8/1996 | Kronner | |
| 5,549,635 A | 8/1996 | Solar | |
| 5,554,181 A | 9/1996 | Das | |
| 5,562,725 A | 10/1996 | Schmitt et al. | |
| 5,571,086 A | 11/1996 | Kaplan et al. | |
| 5,591,195 A | 1/1997 | Taheri et al. | |
| 5,593,412 A | 1/1997 | Martinez et al. | |
| 5,607,444 A | 3/1997 | Lam | |
| 5,607,463 A | 3/1997 | Schwartz et al. | |
| 5,628,755 A | 5/1997 | Heller et al. | |
| 5,628,775 A | 5/1997 | Jackson et al. | |
| 5,634,928 A | 6/1997 | Fischell et al. | |
| 5,639,274 A | 6/1997 | Fischell et al. | |
| 5,662,675 A | 9/1997 | Polanskyj Stockert et al. | |
| 5,662,703 A | 9/1997 | Yurek et al. | |
| 5,670,161 A | 9/1997 | Healy et al. | |
| 5,676,654 A | 10/1997 | Ellis et al. | |
| 5,683,451 A | 11/1997 | Lenker et al. | |
| 5,690,644 A | 11/1997 | Yurek et al. | |
| 5,693,085 A | 12/1997 | Buirge et al. | |
| 5,697,948 A | 12/1997 | Marin et al. | |
| 5,697,971 A | 12/1997 | Fischell et al. | |
| 5,702,418 A | 12/1997 | Ravenscroft | |
| 5,702,419 A | 12/1997 | Berry et al. | |
| 5,709,701 A | 1/1998 | Parodi | |
| 5,716,393 A | 2/1998 | Lindenberg et al. | |
| 5,722,669 A | 3/1998 | Shimizu et al. | |
| 5,723,003 A | 3/1998 | Winston et al. | |
| 5,735,869 A | 4/1998 | Fernandez-Aceytuno | |
| 5,741,323 A | 4/1998 | Pathak et al. | |
| 5,749,848 A | 5/1998 | Jang et al. | |
| 5,749,890 A | 5/1998 | Shaknovich | |
| 5,749,921 A | 5/1998 | Lenker et al. | |
| 5,755,697 A * | 5/1998 | Jones et al. | 604/174 |
| 5,755,772 A | 5/1998 | Evans et al. | |
| 5,755,776 A | 5/1998 | Al-Saadon | |
| 5,755,781 A | 5/1998 | Jayaraman | |
| 5,769,882 A | 6/1998 | Fogarty et al. | |
| 5,772,669 A | 6/1998 | Vrba | |
| 5,776,141 A | 7/1998 | Klein et al. | |
| 5,792,144 A | 8/1998 | Fischell et al. | |
| 5,797,951 A | 8/1998 | Mueller et al. | |
| 5,800,519 A | 9/1998 | Sandock | |
| 5,807,398 A | 9/1998 | Shaknovich | |
| 5,824,040 A | 10/1998 | Cox et al. | |
| 5,824,041 A | 10/1998 | Lenker et al. | |
| 5,833,694 A | 11/1998 | Poncet | |
| 5,836,964 A | 11/1998 | Richter et al. | |
| 5,843,092 A | 12/1998 | Heller et al. | |
| 5,855,563 A | 1/1999 | Kaplan et al. | |
| 5,858,556 A | 1/1999 | Eckert et al. | |
| 5,870,381 A | 2/1999 | Kawasaki et al. | |
| 5,879,370 A | 3/1999 | Fischell et al. | |
| 5,891,190 A | 4/1999 | Boneau | |
| 5,895,398 A | 4/1999 | Wensel et al. | |
| 5,899,935 A | 5/1999 | Ding | |
| 5,902,332 A | 5/1999 | Schatz | |
| 5,919,175 A | 7/1999 | Sirhan | |
| 5,921,971 A * | 7/1999 | Agro et al. | 604/523 |
| 5,922,020 A | 7/1999 | Klein et al. | |
| 5,941,869 A | 8/1999 | Patterson et al. | |
| 5,951,585 A | 9/1999 | Cathcart et al. | |
| 5,961,536 A | 10/1999 | Mickley et al. | |
| 5,968,069 A | 10/1999 | Dusbabek et al. | |
| 5,972,027 A | 10/1999 | Johnson | |
| 5,976,107 A | 11/1999 | Mertens et al. | |
| 5,976,155 A | 11/1999 | Foreman et al. | |
| 5,980,484 A | 11/1999 | Ressemann et al. | |
| 5,980,486 A | 11/1999 | Enger | |
| 5,980,514 A | 11/1999 | Kupiecki et al. | |
| 5,980,552 A | 11/1999 | Pinchasik et al. | |
| 5,984,957 A | 11/1999 | Laptewicz, Jr. et al. | |
| 5,989,280 A | 11/1999 | Euteneuer et al. | |
| 5,993,484 A | 11/1999 | Shmulewitz | |
| 5,997,563 A | 12/1999 | Kretzers et al. | |
| 6,004,328 A | 12/1999 | Solar | |
| 6,007,517 A | 12/1999 | Anderson | |
| 6,010,530 A | 1/2000 | Goicoechea | |
| 6,022,359 A | 2/2000 | Frantzen | |
| 6,022,374 A | 2/2000 | Imran | |
| 6,027,519 A | 2/2000 | Stanford | |
| 6,033,434 A | 3/2000 | Borghi | |
| 6,036,725 A | 3/2000 | Avellanet | |
| 6,039,721 A | 3/2000 | Johnson et al. | |
| 6,042,589 A | 3/2000 | Marianne | |
| 6,056,722 A | 5/2000 | Jayaraman | |
| 6,063,111 A | 5/2000 | Hieshima et al. | |
| 6,066,155 A | 5/2000 | Amann et al. | |
| 6,068,655 A | 5/2000 | Seguin et al. | |
| 6,070,589 A | 6/2000 | Keith et al. | |
| 6,090,063 A | 7/2000 | Makower et al. | |
| 6,090,136 A | 7/2000 | McDonald et al. | |
| 6,102,942 A | 8/2000 | Ahari | |
| 6,106,530 A | 8/2000 | Harada | |
| RE36,857 E | 9/2000 | Euteneuer et al. | |
| 6,120,522 A | 9/2000 | Vrba et al. | |
| 6,123,712 A | 9/2000 | Di Caprio et al. | |
| 6,123,723 A | 9/2000 | Konya et al. | |
| 6,126,685 A | 10/2000 | Lenker et al. | |
| 6,129,756 A | 10/2000 | Kugler | |
| 6,132,460 A | 10/2000 | Thompson | |
| 6,139,572 A | 10/2000 | Campbell et al. | |
| 6,143,016 A | 11/2000 | Bleam et al. | |

| | | |
|---|---|---|
| 6,165,167 A | 12/2000 | Delaloye |
| 6,165,210 A | 12/2000 | Lau et al. |
| 6,171,334 B1 | 1/2001 | Cox |
| 6,179,878 B1 | 1/2001 | Duering |
| 6,183,509 B1 | 2/2001 | Dibie |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,217,585 B1 | 4/2001 | Houser et al. |
| 6,238,991 B1 | 5/2001 | Suzuki |
| 6,241,691 B1 | 6/2001 | Ferrera et al. |
| 6,241,758 B1 | 6/2001 | Cox |
| 6,248,122 B1 | 6/2001 | Klumb et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,264,688 B1 | 7/2001 | Herklotz et al. |
| 6,267,783 B1 | 7/2001 | Letendre et al. |
| 6,270,524 B1 | 8/2001 | Kim |
| 6,273,895 B1 | 8/2001 | Pinchuk et al. |
| 6,273,911 B1 | 8/2001 | Cox et al. |
| 6,273,913 B1 | 8/2001 | Wright et al. |
| 6,287,291 B1 | 9/2001 | Bigus et al. |
| 6,312,458 B1 | 11/2001 | Golds |
| 6,315,794 B1 | 11/2001 | Richter |
| 6,319,277 B1 | 11/2001 | Rudnick et al. |
| 6,322,586 B1 | 11/2001 | Monroe et al. |
| 6,325,823 B1 | 12/2001 | Horzewski et al. |
| 6,334,871 B1 | 1/2002 | Dor et al. |
| 6,340,366 B2 | 1/2002 | Wijay |
| 6,344,272 B1 | 2/2002 | Oldenburg et al. |
| 6,348,065 B1 | 2/2002 | Brown et al. |
| 6,350,252 B2 | 2/2002 | Ray et al. |
| 6,350,277 B1 | 2/2002 | Kocur |
| 6,357,104 B1 | 3/2002 | Myers |
| 6,361,558 B1 | 3/2002 | Hieshima et al. |
| 6,375,676 B1 | 4/2002 | Cox |
| 6,379,365 B1 | 4/2002 | Diaz |
| 6,383,171 B1 | 5/2002 | Gifford et al. |
| 6,394,995 B1 * | 5/2002 | Solar et al. .............. 604/528 |
| 6,409,753 B1 | 6/2002 | Brown et al. |
| 6,415,696 B1 | 7/2002 | Erickson et al. |
| 6,416,543 B1 | 7/2002 | Hilaire et al. |
| 6,419,693 B1 | 7/2002 | Fariabi |
| 6,425,898 B1 | 7/2002 | Wilson et al. |
| 6,428,811 B1 | 8/2002 | West et al. |
| 6,451,025 B1 | 9/2002 | Jervis |
| 6,451,050 B1 | 9/2002 | Rudakov et al. |
| 6,464,720 B2 | 10/2002 | Boatman et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,488,702 B1 | 12/2002 | Besselink |
| 6,511,468 B1 | 1/2003 | Cragg et al. |
| 6,520,986 B2 | 2/2003 | Martin et al. |
| 6,520,987 B1 | 2/2003 | Plante |
| 6,527,789 B1 | 3/2003 | Lau et al. |
| 6,527,799 B2 | 3/2003 | Shanley |
| 6,530,944 B2 | 3/2003 | West et al. |
| 6,540,777 B2 | 4/2003 | Stenzel |
| 6,551,350 B1 | 4/2003 | Thornton et al. |
| 6,555,157 B1 | 4/2003 | Hossainy |
| 6,558,415 B2 | 5/2003 | Thompson |
| 6,562,067 B2 | 5/2003 | Mathis |
| 6,569,180 B1 | 5/2003 | Sirhan et al. |
| 6,575,993 B1 | 6/2003 | Yock |
| 6,579,305 B1 | 6/2003 | Lashinski |
| 6,579,309 B1 | 6/2003 | Loos et al. |
| 6,582,394 B1 | 6/2003 | Reiss et al. |
| 6,582,460 B1 | 6/2003 | Cryer |
| 6,585,756 B1 | 7/2003 | Strecker |
| 6,589,273 B1 | 7/2003 | McDermott |
| 6,592,549 B2 | 7/2003 | Gerdts et al. |
| 6,599,296 B1 | 7/2003 | Gillick et al. |
| 6,599,314 B2 | 7/2003 | Mathis |
| 6,602,226 B1 | 8/2003 | Smith et al. |
| 6,602,282 B1 | 8/2003 | Yan |
| 6,605,062 B1 | 8/2003 | Hurley et al. |
| 6,605,109 B2 | 8/2003 | Fiedler |
| 6,607,553 B1 | 8/2003 | Healy et al. |
| 6,613,074 B1 | 9/2003 | Mitelberg et al. |
| 6,629,992 B2 | 10/2003 | Bigus et al. |
| 6,645,517 B2 | 11/2003 | West |
| 6,645,547 B1 | 11/2003 | Shekalim et al. |
| 6,656,212 B2 | 12/2003 | Ravenscroft et al. |
| 6,660,031 B2 | 12/2003 | Tran et al. |
| 6,660,381 B2 | 12/2003 | Halas et al. |
| 6,663,660 B2 | 12/2003 | Dusbabek et al. |
| 6,666,883 B1 | 12/2003 | Seguin et al. |
| 6,676,693 B1 | 1/2004 | Belding et al. |
| 6,676,695 B2 | 1/2004 | Solem |
| 6,679,909 B2 | 1/2004 | McIntosh et al. |
| 6,685,730 B2 | 2/2004 | West et al. |
| 6,692,465 B2 | 2/2004 | Kramer |
| 6,699,280 B2 | 3/2004 | Camrud et al. |
| 6,699,281 B2 | 3/2004 | Vallana et al. |
| 6,699,724 B1 | 3/2004 | West et al. |
| 6,702,843 B1 | 3/2004 | Brown |
| 6,709,379 B1 | 3/2004 | Brandau et al. |
| 6,709,440 B2 | 3/2004 | Callol et al. |
| 6,712,827 B2 | 3/2004 | Ellis et al. |
| 6,712,845 B2 | 3/2004 | Hossainy |
| 6,723,071 B2 | 4/2004 | Gerdts et al. |
| 6,736,842 B2 | 5/2004 | Healy et al. |
| 6,743,219 B1 | 6/2004 | Dwyer et al. |
| 6,743,251 B1 | 6/2004 | Eder |
| 6,761,734 B2 | 7/2004 | Suhr |
| 6,776,771 B2 | 8/2004 | van Moorlegem et al. |
| 6,778,316 B2 | 8/2004 | Halas et al. |
| 6,790,227 B2 | 9/2004 | Burgermeister |
| 6,800,065 B2 | 10/2004 | Duane et al. |
| 6,825,203 B2 | 11/2004 | Pasternak et al. |
| 6,837,901 B2 | 1/2005 | Rabkin et al. |
| 6,849,084 B2 | 2/2005 | Rabkin et al. |
| 6,852,252 B2 | 2/2005 | Halas et al. |
| 6,855,125 B2 | 2/2005 | Shanley |
| 6,858,034 B1 | 2/2005 | Hijlkema et al. |
| 6,878,161 B2 | 4/2005 | Lenker |
| 6,884,257 B2 | 4/2005 | Cox |
| 6,893,417 B2 | 5/2005 | Gribbons et al. |
| 6,896,695 B2 | 5/2005 | Mueller et al. |
| 6,899,728 B1 | 5/2005 | Phillips et al. |
| 6,913,619 B2 | 7/2005 | Brown et al. |
| 6,918,928 B2 | 7/2005 | Wolinsky et al. |
| 6,939,376 B2 | 9/2005 | Shulze et al. |
| 6,945,989 B1 | 9/2005 | Betelia et al. |
| 6,945,995 B2 | 9/2005 | Nicholas |
| 6,951,053 B2 | 10/2005 | Padilla et al. |
| 6,962,603 B1 | 11/2005 | Brown et al. |
| 6,964,676 B1 | 11/2005 | Gerberding et al. |
| 6,991,646 B2 | 1/2006 | Clerc et al. |
| 6,994,721 B2 | 2/2006 | Israel |
| 7,005,454 B2 | 2/2006 | Brocchini et al. |
| 7,022,132 B2 | 4/2006 | Kocur |
| 7,029,493 B2 | 4/2006 | Majercak et al. |
| 7,037,327 B2 | 5/2006 | Salmon et al. |
| 7,090,694 B1 | 8/2006 | Morris et al. |
| 7,101,840 B2 | 9/2006 | Brocchini et al. |
| 7,131,993 B2 | 11/2006 | Gregorich |
| 7,137,993 B2 | 11/2006 | Acosta et al. |
| 7,141,063 B2 | 11/2006 | White et al. |
| 7,147,655 B2 | 12/2006 | Chermoni |
| 7,147,656 B2 | 12/2006 | Andreas et al. |
| 7,169,172 B2 | 1/2007 | Levine et al. |
| 7,169,174 B2 | 1/2007 | Fischell et al. |
| 7,172,620 B2 | 2/2007 | Gilson |
| 7,175,654 B2 | 2/2007 | Bonsignore et al. |
| 7,182,779 B2 | 2/2007 | Acosta et al. |
| 7,192,440 B2 | 3/2007 | Andreas et al. |
| 7,208,001 B2 | 4/2007 | Coyle et al. |
| 7,208,002 B2 | 4/2007 | Shelso |
| 7,220,275 B2 | 5/2007 | Davidson et al. |
| 7,220,755 B2 | 5/2007 | Betts et al. |
| 7,223,283 B2 | 5/2007 | Chouinard |

| | | |
|---|---|---|
| 7,238,197 B2 | 7/2007 | Sequin et al. |
| 7,241,308 B2 | 7/2007 | Andreas et al. |
| 7,244,336 B2 | 7/2007 | Fischer et al. |
| 7,270,668 B2 | 9/2007 | Andreas et al. |
| 7,294,146 B2 | 11/2007 | Chew et al. |
| 7,300,456 B2 | 11/2007 | Andreas et al. |
| 7,309,350 B2 | 12/2007 | Landreville et al. |
| 7,314,480 B2 | 1/2008 | Eidenschink et al. |
| 7,320,702 B2 | 1/2008 | Hammersmark et al. |
| 7,323,006 B2 | 1/2008 | Andreas et al. |
| 7,326,236 B2 | 2/2008 | Andreas et al. |
| 7,534,449 B2 | 5/2009 | Saltzman et al. |
| 7,699,886 B2 | 4/2010 | Sugimoto |
| 7,918,881 B2 | 4/2011 | Andreas et al. |
| 7,993,388 B2 | 8/2011 | Lee et al. |
| 8,257,427 B2 | 9/2012 | Andersen et al. |
| 8,317,850 B2 | 11/2012 | Kusleika |
| 2001/0020154 A1 | 9/2001 | Bigus et al. |
| 2001/0020173 A1 | 9/2001 | Klumb et al. |
| 2001/0020181 A1 | 9/2001 | Layne |
| 2001/0035902 A1 | 11/2001 | Iddan et al. |
| 2001/0044595 A1 | 11/2001 | Reydel et al. |
| 2001/0044632 A1 | 11/2001 | Daniel et al. |
| 2001/0049547 A1 | 12/2001 | Moore |
| 2002/0007212 A1 | 1/2002 | Brown et al. |
| 2002/0032457 A1* | 3/2002 | Sirhan et al. .................. 606/195 |
| 2002/0037358 A1 | 3/2002 | Barry et al. |
| 2002/0045914 A1 | 4/2002 | Roberts et al. |
| 2002/0052642 A1 | 5/2002 | Cox et al. |
| 2002/0087186 A1 | 7/2002 | Shelso |
| 2002/0091439 A1 | 7/2002 | Baker et al. |
| 2002/0092536 A1 | 7/2002 | LaFontaine et al. |
| 2002/0107560 A1 | 8/2002 | Richter |
| 2002/0111671 A1 | 8/2002 | Stenzel |
| 2002/0123786 A1 | 9/2002 | Gittings et al. |
| 2002/0128706 A1 | 9/2002 | Ospyka |
| 2002/0138132 A1 | 9/2002 | Brown |
| 2002/0151924 A1 | 10/2002 | Shiber |
| 2002/0151955 A1 | 10/2002 | Tran et al. |
| 2002/0156496 A1 | 10/2002 | Chermoni |
| 2002/0165599 A1 | 11/2002 | Nasralla |
| 2002/0168317 A1 | 11/2002 | Daighighian et al. |
| 2002/0177890 A1 | 11/2002 | Lenker |
| 2002/0183763 A1 | 12/2002 | Callol et al. |
| 2002/0188343 A1 | 12/2002 | Mathis |
| 2002/0188347 A1 | 12/2002 | Mathis |
| 2002/0193873 A1 | 12/2002 | Brucker et al. |
| 2003/0045923 A1 | 3/2003 | Bashiri et al. |
| 2003/0093143 A1 | 5/2003 | Zhao et al. |
| 2003/0097169 A1 | 5/2003 | Brucker et al. |
| 2003/0114912 A1 | 6/2003 | Sequin et al. |
| 2003/0114919 A1 | 6/2003 | McQuiston et al. |
| 2003/0114922 A1 | 6/2003 | Iwasaka et al. |
| 2003/0125791 A1 | 7/2003 | Sequin et al. |
| 2003/0125800 A1 | 7/2003 | Shulze et al. |
| 2003/0125802 A1 | 7/2003 | Callol et al. |
| 2003/0135259 A1 | 7/2003 | Simso |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0139798 A1 | 7/2003 | Brown et al. |
| 2003/0163085 A1 | 8/2003 | Tanner et al. |
| 2003/0163155 A1 | 8/2003 | Haverkost et al. |
| 2003/0176909 A1 | 9/2003 | Kusleika |
| 2003/0191516 A1 | 10/2003 | Weldon et al. |
| 2003/0195609 A1 | 10/2003 | Berenstein |
| 2003/0199821 A1 | 10/2003 | Gerdts et al. |
| 2003/0204238 A1 | 10/2003 | Tedeschi |
| 2003/0208223 A1 | 11/2003 | Kleiner |
| 2003/0212447 A1 | 11/2003 | Euteneuer et al. |
| 2003/0225446 A1 | 12/2003 | Hartley |
| 2004/0015224 A1 | 1/2004 | Armstrong et al. |
| 2004/0024450 A1 | 2/2004 | Shulze et al. |
| 2004/0030380 A1 | 2/2004 | Shulze et al. |
| 2004/0044395 A1 | 3/2004 | Nelson |
| 2004/0073290 A1 | 4/2004 | Chouinard |
| 2004/0088044 A1 | 5/2004 | Brown et al. |
| 2004/0093061 A1 | 5/2004 | Acosta et al. |
| 2004/0093067 A1 | 5/2004 | Israel |
| 2004/0106979 A1 | 6/2004 | Goicoechea et al. |
| 2004/0111145 A1 | 6/2004 | Serino et al. |
| 2004/0117008 A1 | 6/2004 | Wnendt et al. |
| 2004/0143322 A1 | 7/2004 | Litvack et al. |
| 2004/0176832 A1 | 9/2004 | Hartley et al. |
| 2004/0181239 A1 | 9/2004 | Dorn et al. |
| 2004/0186551 A1 | 9/2004 | Kao et al. |
| 2004/0193245 A1 | 9/2004 | Deem et al. |
| 2004/0215165 A1 | 10/2004 | Coyle et al. |
| 2004/0215312 A1 | 10/2004 | Andreas |
| 2004/0215331 A1 | 10/2004 | Chew et al. |
| 2004/0230285 A1 | 11/2004 | Gifford, III et al. |
| 2004/0243217 A1 | 12/2004 | Andersen et al. |
| 2004/0249434 A1 | 12/2004 | Andreas et al. |
| 2004/0249439 A1 | 12/2004 | Richter et al. |
| 2005/0004657 A1 | 1/2005 | Burgermeister |
| 2005/0010276 A1 | 1/2005 | Acosta et al. |
| 2005/0038494 A1 | 2/2005 | Eidenschink |
| 2005/0038505 A1 | 2/2005 | Shulze et al. |
| 2005/0049673 A1 | 3/2005 | Andreas et al. |
| 2005/0080474 A1 | 4/2005 | Andreas et al. |
| 2005/0080475 A1 | 4/2005 | Andreas et al. |
| 2005/0085897 A1 | 4/2005 | Bonsignore |
| 2005/0090846 A1 | 4/2005 | Pedersen et al. |
| 2005/0123451 A1 | 6/2005 | Nomura |
| 2005/0125051 A1 | 6/2005 | Eidenschink et al. |
| 2005/0131008 A1 | 6/2005 | Betts et al. |
| 2005/0137622 A1 | 6/2005 | Griffin |
| 2005/0143827 A1 | 6/2005 | Globerman et al. |
| 2005/0149168 A1 | 7/2005 | Gregorich |
| 2005/0165378 A1 | 7/2005 | Heinrich et al. |
| 2005/0171568 A1* | 8/2005 | Duffy ............................ 606/191 |
| 2005/0182477 A1 | 8/2005 | White |
| 2005/0209674 A1 | 9/2005 | Kutscher et al. |
| 2005/0209676 A1 | 9/2005 | Kusleika |
| 2005/0209680 A1 | 9/2005 | Gale et al. |
| 2005/0222671 A1 | 10/2005 | Schaeffer et al. |
| 2005/0228477 A1 | 10/2005 | Grainger et al. |
| 2005/0245637 A1 | 11/2005 | Hossainy et al. |
| 2005/0249777 A1 | 11/2005 | Michal et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0173529 A1 | 8/2006 | Blank |
| 2006/0200223 A1 | 9/2006 | Andreas et al. |
| 2006/0206190 A1 | 9/2006 | Chermoni |
| 2006/0229700 A1 | 10/2006 | Acosta et al. |
| 2006/0229706 A1 | 10/2006 | Shulze et al. |
| 2006/0271150 A1 | 11/2006 | Andreas et al. |
| 2006/0271151 A1 | 11/2006 | McGarry et al. |
| 2006/0282147 A1 | 12/2006 | Andreas et al. |
| 2006/0282149 A1 | 12/2006 | Kao |
| 2006/0282150 A1 | 12/2006 | Olson et al. |
| 2006/0287726 A1 | 12/2006 | Segal et al. |
| 2007/0010869 A1 | 1/2007 | Sano |
| 2007/0027521 A1 | 2/2007 | Andreas et al. |
| 2007/0043419 A1 | 2/2007 | Nikolchev et al. |
| 2007/0067012 A1 | 3/2007 | George et al. |
| 2007/0088368 A1 | 4/2007 | Acosta et al. |
| 2007/0088420 A1 | 4/2007 | Andreas et al. |
| 2007/0088422 A1 | 4/2007 | Chew et al. |
| 2007/0100423 A1 | 5/2007 | Acosta et al. |
| 2007/0100424 A1 | 5/2007 | Chew et al. |
| 2007/0106365 A1 | 5/2007 | Andreas et al. |
| 2007/0118202 A1 | 5/2007 | Chermoni |
| 2007/0118203 A1 | 5/2007 | Chermoni |
| 2007/0118204 A1 | 5/2007 | Chermoni |
| 2007/0129733 A1 | 6/2007 | Will et al. |
| 2007/0135906 A1 | 6/2007 | Badylak et al. |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0219612 A1 | 9/2007 | Andreas et al. |
| 2007/0219613 A1 | 9/2007 | Kao et al. |
| 2007/0265637 A1 | 11/2007 | Andreas et al. |
| 2007/0270936 A1 | 11/2007 | Andreas et al. |
| 2007/0276461 A1 | 11/2007 | Andreas et al. |
| 2007/0281117 A1 | 12/2007 | Kaplan et al. |

| | | | |
|---|---|---|---|
| 2007/0292518 A1 | 12/2007 | Ludwig | |
| 2008/0004690 A1 | 1/2008 | Robaina | |
| 2008/0046067 A1 | 2/2008 | Toyokawa | |
| 2008/0071345 A1 | 3/2008 | Hammersmark et al. | |
| 2008/0077229 A1 | 3/2008 | Andreas et al. | |
| 2008/0097574 A1 | 4/2008 | Andreas et al. | |
| 2008/0125850 A1 | 5/2008 | Andreas et al. | |
| 2008/0147162 A1 | 6/2008 | Andreas et al. | |
| 2008/0177369 A1 | 7/2008 | Will et al. | |
| 2008/0199510 A1 | 8/2008 | Ruane et al. | |
| 2008/0208311 A1 | 8/2008 | Kao et al. | |
| 2008/0208318 A1 | 8/2008 | Kao et al. | |
| 2008/0234795 A1 | 9/2008 | Snow et al. | |
| 2008/0234798 A1 | 9/2008 | Chew et al. | |
| 2008/0234799 A1 | 9/2008 | Acosta et al. | |
| 2008/0243225 A1 | 10/2008 | Satasiya et al. | |
| 2008/0249607 A1 | 10/2008 | Webster et al. | |
| 2008/0269865 A1 | 10/2008 | Snow et al. | |
| 2009/0076584 A1 | 3/2009 | Mao et al. | |
| 2009/0105686 A1 | 4/2009 | Snow et al. | |
| 2009/0149863 A1 | 6/2009 | Andreas et al. | |
| 2009/0234428 A1 | 9/2009 | Snow et al. | |
| 2009/0248137 A1 | 10/2009 | Andersen et al. | |
| 2009/0248140 A1 | 10/2009 | Gerberding | |
| 2009/0264979 A1 | 10/2009 | Kao et al. | |
| 2009/0276030 A1 | 11/2009 | Kusleika | |
| 2010/0004729 A1 | 1/2010 | Chew et al. | |

FOREIGN PATENT DOCUMENTS

| | | |
|---|---|---|
| DE | 199 50 756 | 8/2000 |
| DE | 101 03 000 | 8/2002 |
| EP | 0 203 945 B2 | 12/1986 |
| EP | 0 274 129 B1 | 7/1988 |
| EP | 0 282 143 | 9/1988 |
| EP | 0 364 787 A1 | 4/1990 |
| EP | 0 505 686 | 9/1992 |
| EP | 0 533 960 | 3/1993 |
| EP | 0 696 447 A2 | 2/1996 |
| EP | 0 714 640 | 6/1996 |
| EP | 0 596 145 | 5/1997 |
| EP | 0 797 963 A2 | 10/1997 |
| EP | 0 947 180 | 10/1999 |
| EP | 1 254 644 A1 | 11/2002 |
| EP | 1 258 230 | 11/2002 |
| EP | 1 277 449 | 1/2003 |
| EP | 1 290 987 A2 | 3/2003 |
| EP | 1 318 765 | 6/2003 |
| EP | 1 470 834 | 10/2004 |
| EP | 1 523 959 A2 | 4/2005 |
| EP | 1 523 960 A2 | 4/2005 |
| EP | 1 266 638 B1 | 10/2005 |
| GB | 2277875 A | 11/1994 |
| JP | 03-133446 | 6/1991 |
| JP | 07-132148 | 5/1995 |
| JP | 10-503663 | 4/1998 |
| JP | 10-295823 | 11/1998 |
| JP | 11-503056 T | 3/1999 |
| JP | 2001-190687 | 7/2001 |
| JP | 2002-538932 T | 11/2002 |
| JP | 2004-121343 A | 4/2004 |
| WO | 94/27667 A1 | 12/1994 |
| WO | WO 95/26695 A2 | 10/1995 |
| WO | 95/29647 A2 | 11/1995 |
| WO | 96/26689 | 9/1996 |
| WO | WO 96/33677 | 10/1996 |
| WO | 96/37167 A1 | 11/1996 |
| WO | WO 96/39077 | 12/1996 |
| WO | 97/10778 | 3/1997 |
| WO | WO 97/46174 | 12/1997 |
| WO | WO 97/48351 | 12/1997 |
| WO | 98/20810 | 5/1998 |
| WO | WO 98/37833 | 9/1998 |
| WO | 98/58600 | 12/1998 |
| WO | WO 99/01087 | 1/1999 |
| WO | 99/65421 | 12/1999 |
| WO | WO 00/12832 A3 | 3/2000 |
| WO | WO 00/15151 | 3/2000 |
| WO | 00/25841 | 5/2000 |
| WO | WO 00/32136 | 6/2000 |
| WO | WO 00/41649 | 7/2000 |
| WO | WO 00/50116 | 8/2000 |
| WO | 00/51525 A1 | 9/2000 |
| WO | WO 00/56237 | 9/2000 |
| WO | WO 00/62708 | 10/2000 |
| WO | WO 00/72780 | 12/2000 |
| WO | 01/26707 | 4/2001 |
| WO | 01/34063 | 5/2001 |
| WO | WO 01/70297 | 9/2001 |
| WO | WO 01/91918 | 12/2001 |
| WO | 02/071975 | 9/2002 |
| WO | WO 02/085253 | 10/2002 |
| WO | WO 02/098326 | 12/2002 |
| WO | WO 03/022178 | 3/2003 |
| WO | WO 03/047651 | 6/2003 |
| WO | WO 03/051425 | 6/2003 |
| WO | WO 03/075797 | 9/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 A2 | 6/2004 |
| WO | 2004/087006 | 10/2004 |
| WO | 2004/091441 | 10/2004 |
| WO | 2005/013853 | 2/2005 |
| WO | WO 2005/009295 | 2/2005 |
| WO | 2005/023153 | 3/2005 |
| WO | 2006/036939 | 4/2006 |
| WO | 2006/047520 | 5/2006 |
| WO | 2007/035805 | 3/2007 |
| WO | WO 2007/053187 | 5/2007 |
| WO | 2007/146411 | 12/2007 |
| WO | 2008/005111 | 1/2008 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Evans Analytical Group, "Functional Sites on Non-polymeric Materials: Gas Plasma Treatment and Surface Analysis," http://www.eaglabs.com.

Joung et al., "Estrogen Release from Metallic Stent Surface for the Prevention of Restenosis," Journal of Controlled Release 92 (2003) pp. 83-91.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al., Parallel Production of Oligonucleotide Arrays Using Membranes and Reagent Jet Printing, BioTechniques 25:886-890 (Nov. 1998).

U.S. Appl. No. 60/336,607, filed Dec. 3, 2001, first named inventor: Bernard Andreas.

U.S. Appl. No. 60/336,767, filed Dec. 3, 2001, first named inventor: Bernard Andreas.

U.S. Appl. No. 60/336,967, filed Dec. 3, 2001, first named inventor: Sunmi Chew.

U.S. Appl. No. 60/364,389, filed Mar. 13, 2002, first named inventor: Sunmi Chew.

U.S. Appl. No. 60/440,839, filed Jan. 17, 2003, first named inventor: Bernard Andreas.

U.S. Appl. No. 60/561,041, filed Apr. 9, 2004, first named inventor: Jeffry Grainger.

U.S. Appl. No. 60/784,309, filed Mar. 20, 2006, first named inventor: Bernard Andreas.

U.S. Appl. No. 60/810,522, filed Jun. 2, 2006, first named inventor: Stephen Kaplan.

U.S. Appl. No. 60/890,703, filed Feb. 20, 2007, first named inventor: Patrick Ruane.

U.S. Appl. No. 61/012,317, filed Dec. 7, 2007, first named inventor: Patrick Ruane.

U.S. Appl. No. 09/097,855, filed Jun. 15, 1998, first named inventor: Enrique J. Klein.

U.S. Appl. No. 09/225,364, filed Jan. 4, 1999, first named inventor: Aaron V. Kaplan.
U.S. Appl. No. 10/874,859, filed Jun. 22, 2004, first named inventor: Pablo Acosta. Abandoned.
U.S. Appl. No. 11/462,951, filed Aug. 7, 2006, first named inventor: David Snow.
U.S. Appl. No. 11/627,096, filed Jan. 25, 2007, first named inventor: Bernard Andreas.
U.S. Appl. No. 11/689,927, filed Mar. 22, 2007, first named inventor: David Snow.
U.S. Appl. No. 11/752,448, filed May 23, 2007, first named inventor: David Snow.
U.S. Appl. No. 11/771,929, filed Jun. 29, 2007, first named inventor: David Snow.
U.S. Appl. No. 11/857,562, filed Sep. 19, 2007, first named inventor: Bryan Mao.
U.S. Appl. No. 11/938,730, filed Nov. 12, 2007, first named inventor: Sunmi Chew.
U.S. Appl. No. 11/945,142, filed Nov. 26, 2007, first named inventor: Bernard Andreas.
U.S. Appl. No. 11/947,677, filed Nov. 29, 2007, first named inventor: Dan Hammersmark.
U.S. Appl. No. 11/953,242, filed Dec. 10, 2007, first named inventor: Bernard Andreas.
U.S. Appl. No. 12/033,586, filed Feb. 19, 2008, first named inventor: Patrick H. Ruane.
U.S. Appl. No. 12/040,598, filed Feb. 29, 2008, first named inventor: Bernard Andreas.
"Drug Delivery Stent With Holes Located on Neutral Axis" Research Disclosure, Kenneth Mason Publications, Hampshire, CB, No. 429, Jan. 2000, p. 13.
Office Action and English Translation of Japanese Patent Application No. 2007-506576, mailed Jul. 13, 2010, 6 pages total.
Chu et al., "Preparation of Thermo-Responsive Core-Shell Microcapsules with a Porous Membrane and Poly(N-isopropylacrylamide) Gates," J Membrane Sci, Oct. 15, 2001; 192(1-2):27-39.
Tilley , "Biolimus A9-Eluting Stent Shows Promise," Medscape Medical News, Oct. 5, 2004; retrieved from the internet: <http://www.medscape.com/viewarticle/490621>, 2 pages total.
Weir et al., "Degradation of poly-L-lactide. Part 2: increased temperature accelerated degradation," Proc Inst Mech Eng H. 2004;218(5):321-30.
Supplementary European Search Report of EP Patent Application No. 05727731.1, dated Mar. 25, 2008, 2 pages total.
Supplementary European Search Report of EP Patent Application No. 05744136, dated Mar. 26, 2008, 3 pages total.
Supplementary European Search Report of EP Patent Application No. 07758831, dated Dec. 14, 2009.

* cited by examiner

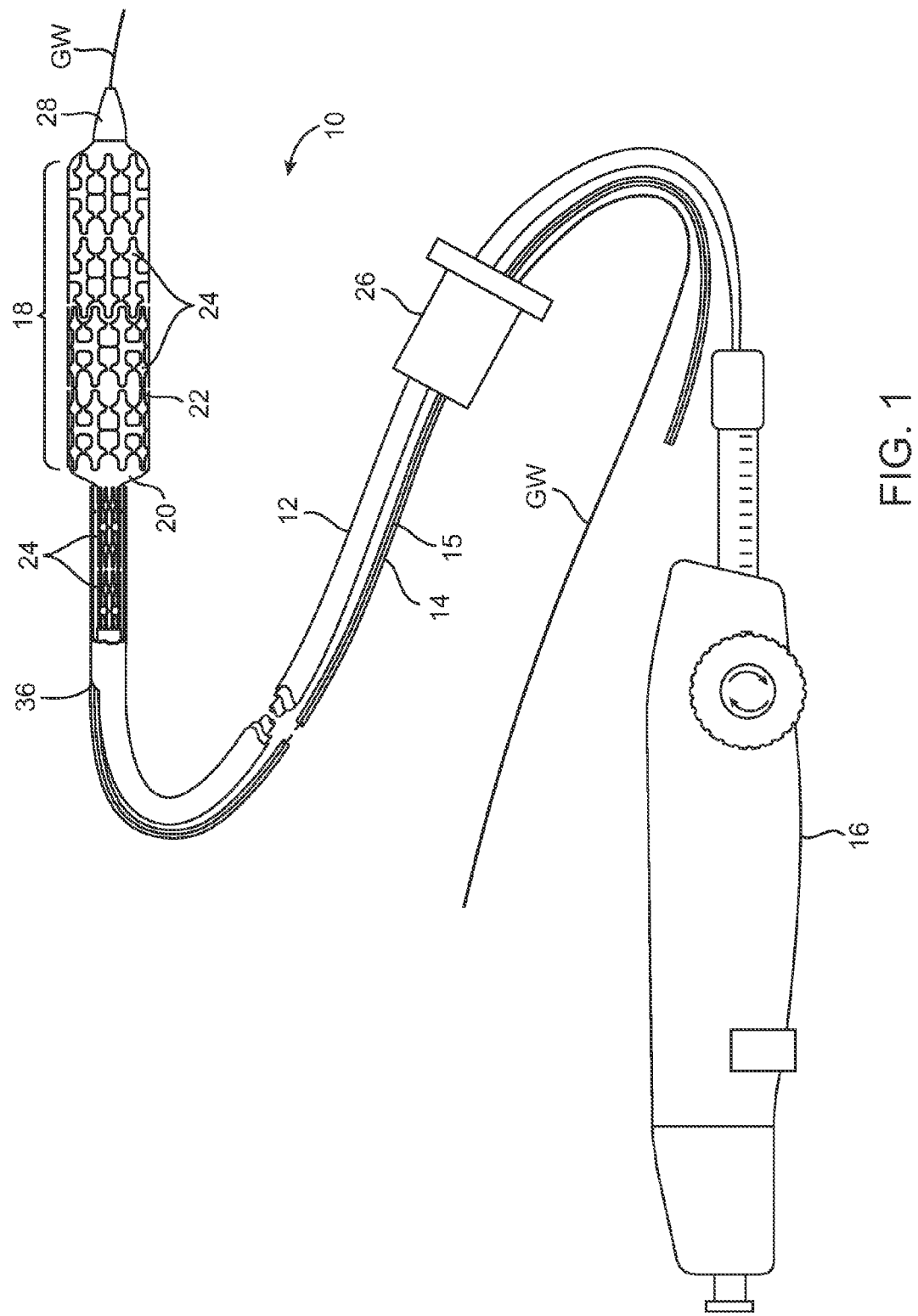

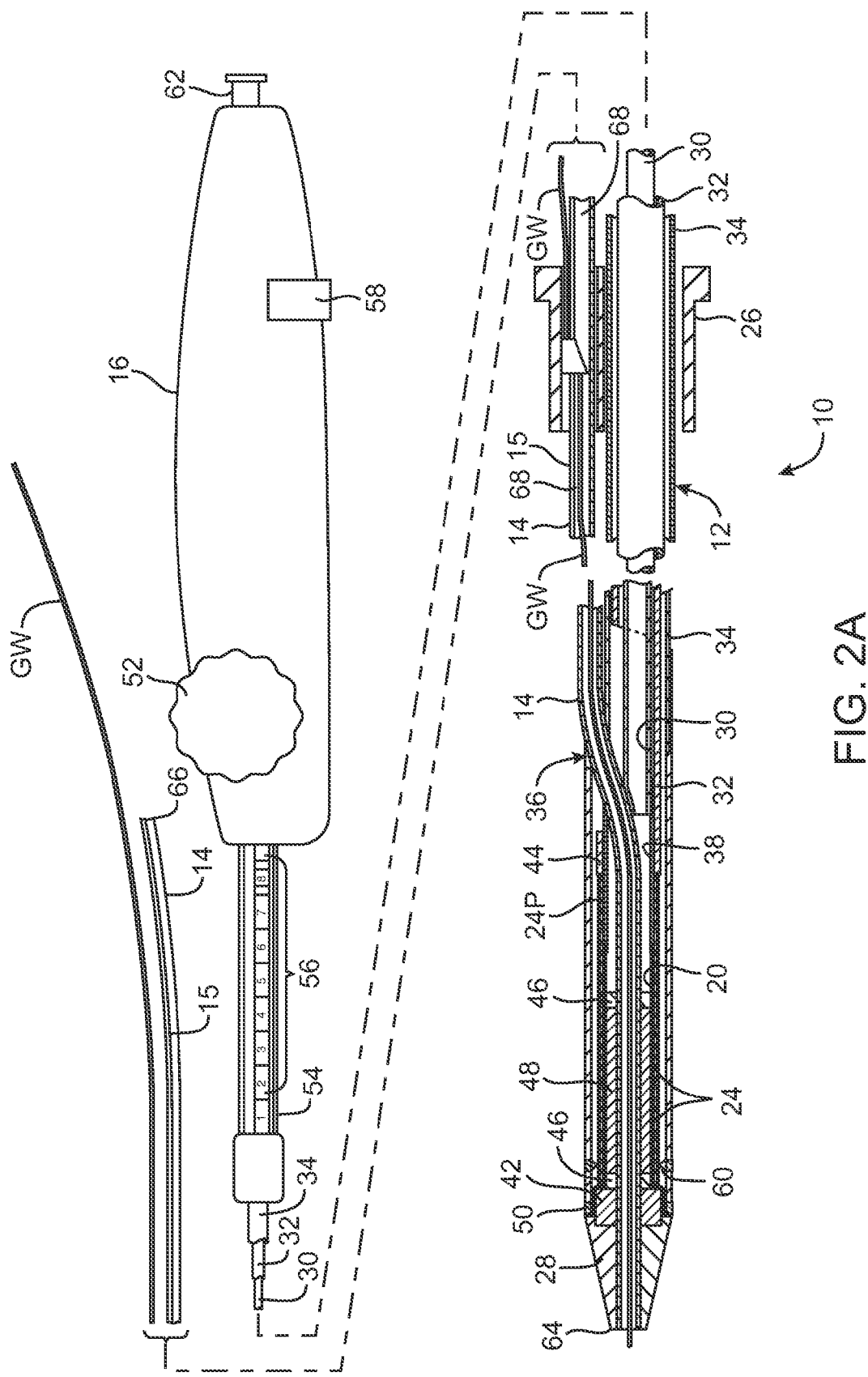

RAPID EXCHANGE INTERVENTIONAL DEVICES AND METHODS

CROSS-REFERENCES TO RELATED APPLICATIONS

The present application is a divisional of U.S. application Ser. No. 10/814,581, filed Mar. 30, 2004, (now U.S. Pat. No. 7,323,006 issued Jan. 29, 2008) the full disclosure of which is incorporated herein by reference.

BACKGROUND OF THE INVENTION

The use of wire-guided catheter interventions for diagnosis and treatment of disease is increasing dramatically. Such interventions are employed in the arterial and venous vasculature, in the heart, kidneys, liver, and other organs, in the stomach, intestines, and urinary tract, in the trachea and lungs, in the uterus, ovaries and fallopian tubes, and elsewhere. As new miniaturized and less-invasive technologies are developed, the challenge becomes one of gaining access to the anatomical regions that could benefit from new forms of diagnosis and treatment. Wire-guided catheters provide a proven, minimally-invasive approach to reaching remote regions of the body and performing diagnostic and treatment procedures with precision, safety, and reliability.

A particularly well-known use of wire-guided catheters is for the treatment of coronary artery disease. In coronary artery disease, one or more coronary arteries becomes partially or fully occluded by the build-up of stenotic plaque, slowing or completely blocking blood flow to the heart muscle. If the heart muscle is deprived of blood, a myocardial infarction results, destroying heart muscle tissue and potentially leading to death.

Various coronary interventions have been developed to treat coronary artery disease. Angioplasty involves the use of a balloon catheter that is introduced into a peripheral artery and advanced over a guidewire to the target coronary artery. A balloon on the end of the catheter is expanded within the stenotic lesion to widen the coronary lumen and restore patency. It has been found, however, that in more than 30% of cases, restenosis occurs to again block the artery 6-12 months after angioplasty. To address this issue, coronary stents have been developed, tubular wire mesh scaffolds that are delivered via catheter to the coronary lesion and expanded into engagement with the wall of the artery to maintain its patency. While bare metal stents also experience a significant incidence of restenosis, the use of drug-coated stents in recent years has demonstrated a dramatic reduction in restenosis rates. Angioplasty and stents are also utilized in other vascular regions, including the femoral, iliac, carotid, and other peripheral arteries, as well as in the venous system.

Guidewires are commonly used to facilitate delivery of angioplasty and stent delivery catheters through the vasculature to the target lesion to be treated. Such guidewires are inserted through a vascular access site, usually a puncture, incision or other penetration in a peripheral artery such as a femoral or iliac artery. A guiding catheter is often used to cannulate the ostium of the left or right coronary artery, and the guidewire and other catheters are then introduced through the guiding catheter. Such guiding catheters typically include a hemostasis valve to facilitate insertion and withdrawal of devices while providing a hemostatic seal around the periphery of such devices to minimize blood loss.

The proximal end of the guidewire outside the body is threaded through a guidewire lumen in the delivery catheter to be used. If the catheter is an "over-the-wire" type, the guidewire lumen typically extends through the catheter shaft from the distal tip of the catheter to its proximal end. The disadvantage of such designs is that the guidewire must be very long in order to extend entirely through the catheter while the distal end of the guidewire remains positioned at the target lesion. Further, the process of exchanging catheters (withdrawing a first catheter from the guidewire and replacing it with a second catheter) is challenging and time-consuming with over-the-wire designs because in the region of the vascular penetration, the guidewire is covered by the catheter being withdrawn until the catheter has been completely removed from the patient, preventing the physician from keeping hold of the guidewire and requiring the use of an assistant to hold the proximal end of the guidewire some distance from the patient.

In response to these challenges with over-the-wire catheters, various types of "rapid exchange" catheters have been developed. In one design, the catheter has a shortened guidewire lumen that extends from the distal tip of the catheter to a point a short distance proximal to the balloon, stent, or other interventional element. This permits the use of a substantially shorter guidewire because the proximal end of the guidewire can emerge from the guidewire lumen a relatively short distance from the distal end of the catheter. This design facilitates faster and easier catheter exchanges because the shorter wire is easier to manage and keep sterile, and the shorter guidewire lumen allows the physician to maintain hold on the guidewire as the first catheter is withdrawn and a second is replaced. Examples are seen in U.S. Pat. Nos. 4,762, 129, 5,980,484, 6,165,167, 5,496,346, 5,980,486, and 5,040, 548.

In an alternative design, a guidewire lumen is provided through the catheter shaft from its distal end to the proximal end or to a point a substantial distance from the distal end, as in over-the-wire designs. However, the catheter wall has a longitudinal slit in communication with the guidewire lumen over all or a portion of its length. This allows the proximal end of the guidewire to exit the guidewire lumen through the slit at any of various locations along the length of the catheter. In some designs, the guidewire is threaded through a zipper-like device that slides along the longitudinal slit to insert or remove the guidewire from the guidewire lumen. Examples are seen in U.S. Pat. Nos. 6,527,789, 5,334,187, 6,692,465, Re 36,587, and U.S. Pat. No. 4,988,356.

While rapid exchange catheters have many advantages over over-the-wire designs, current rapid exchange catheters suffer from certain drawbacks. For example, in those rapid exchange designs having a shortened guidewire lumen, the guidewire is exposed outside of the catheter and runs alongside the catheter for a substantial distance within the vessel from the vascular access site to the point at which the guidewire enters the guidewire lumen. In "zipper" type designs, while the guidewire may be enclosed within the catheter in the vessel, the guidewire lumen is integral to the catheter shaft between the distal and proximal ends thereof, increasing its profile and stiffness.

For these and other reasons, improved interventional devices with rapid exchange capabilities are desired. The interventional devices should provide the benefits of conventional rapid exchange catheters, including allowing the use of shorter guidewires and facilitating catheter exchanges by allowing the physician to continually hold and manipulate the guidewire from a position near the vascular access site as a catheter is withdrawn and replaced. Further, the interventional devices should keep the guidewire fully enclosed in the guidewire lumen within the vessel between the vascular access site and the catheter balloon, stent, or other interventional element on the catheter. Additionally, the interventional devices should have a shaft of minimal profile and stiffness in its proximal extremity.

BRIEF SUMMARY OF THE INVENTION

The present invention provides interventional devices and methods for performing vascular interventions that facilitate the use of shorter guidewires, and more rapid exchange of catheters, and provide other advantages over conventional rapid exchange catheters. While the devices and methods of the invention are described primarily in the context of interventions in the arterial system, and particularly in the coronary arteries, the invention will find use in a variety of interventional devices used in various anatomical regions, including peripheral arteries, carotid arteries, veins and vein grafts, vascular grafts, organs such as the heart, liver, and kidneys, intestinal and urinary vessels, the lungs, the uterus, ovaries and fallopian tubes, and other regions in which wire-guided devices are utilized. Such devices include balloon catheters for angioplasty, vascular occlusion, valvuloplasty, and other purposes, stent delivery catheters, angiography catheters, intravascular ultrasound devices, drug delivery catheters, endoscopes, bronchoscopes, and other visualization devices, RF mapping and ablation catheters, valve replacement and repair catheters, catheters for delivery of implantable devices, defect repair catheters, and other devices.

In a first aspect, the invention provides an interventional device for introduction through a vascular penetration to a treatment site in a vessel comprising a catheter shaft having a proximal extremity, a distal extremity and an interventional element coupled to the distal extremity; and a guidewire tube having a proximal end, a distal end and a guidewire lumen therebetween configured to slidably receive a guidewire, the distal end being coupled to the distal extremity of the catheter shaft and the proximal end being separate from the catheter shaft; wherein the proximal extremity of the catheter shaft and the guidewire tube each have a length sufficient to extend to the vascular penetration when the interventional device is positioned at the treatment site.

In a further aspect of the invention, the interventional device includes a collar positionable in the vascular penetration and having at least one passage therein configured to slidably receive the proximal extremity of the catheter shaft and the guidewire without substantial leakage of blood therethrough. The collar is positionable through a hemostatic device in the vascular penetration, the collar having an exterior surface configured to seal within the hemostatic device. The hemostatic device may comprise a rotating hemostasis valve (RHV) or other suitable device for introducing catheters into a vessel with minimal leakage of blood. The collar may further include a seal in communication with the at least one passage for inhibiting leakage of blood around the proximal extremity. In some embodiments, the collar comprises a first passage for receiving the catheter shaft and a second passage for receiving the guidewire tube. In other embodiments, a single passage is provided that receives both the catheter shaft and the guidewire tube.

In another aspect of the invention, the guidewire tube comprises a slit disposed longitudinally therein from a distal point less than about 50 cm from the distal end to a proximal point at least about one-half the length of the guidewire tube from the distal end. The proximal point is usually within about 20 cm from the proximal end of the guidewire tube and may be at the proximal end itself. The interventional device may further include a wire guide positionable through the slit and operative upon the guidewire such that the guidewire is disposed in the guidewire lumen distal to the wire guide and disposed outside the guidewire lumen proximal to the wire guide. The wire guide may be coupled to a collar having at least one passage configured to slidably receive the proximal extremity of the catheter shaft and the guidewire tube. The wire guide preferably comprises a distal opening, a proximal opening, and a guide passage therebetween, the distal opening being aligned with the guidewire lumen and the proximal opening being outside the guidewire tube when the wire guide is positioned through the slit. The wire guide may further have a rounded or tapered distal edge configured to spread the slit in the guidewire tube.

In still another aspect of the invention, the guidewire tube is collapsible from an extended length to a collapsed length. In exemplary embodiments, the extended length is at least about 140 cm and the collapsed length is no more than about 30 cm. In these embodiments, the guidewire tube may have any of various collapsible and extendable structures, including an accordion-like wall with a zig-zag cross-section. The guidewire tube may also have a series of generally conical segments connected by hinges, whereby adjacent conical segments are pivotable toward and away from each other about the hinges. The conical or dome-shaped segments may also be configured to nest within one another in the collapsed configuration. Preferably, a collar is provided having at least one passage configured to slidably receive the proximal extremity of the catheter shaft. The proximal end of the guidewire tube is coupled to the collar such that moving the catheter shaft relative to the collar extends or retracts the guidewire tube.

In preferred embodiments, the interventional element comprises a stent. The stent may have a plurality of stent segments. The interventional device may also include a sheath slidably disposed over the stent segments. The sheath may be selectively positioned to deploy a first selected number of stent segments from the catheter shaft while retaining a second selected number of stent segments on the catheter shaft. The interventional element may also comprise an expandable member such as a balloon. Again, a sheath may be slidably disposed over the balloon and selectively positioned to expand a first portion of the balloon while constraining a second portion of the balloon. In some embodiments, the guidewire tube couples with the catheter shaft proximal to the interventional element and extends to a point distal to the interventional element.

The invention further provides methods of performing diagnostic and therapeutic interventions using wire-guided devices. In a first aspect, a method of performing an intervention at a treatment site through a vascular penetration in a vessel comprises providing an interventional device having a catheter shaft, an interventional element coupled to a distal extremity of the catheter shaft, and a guidewire tube having a distal portion coupled to the distal extremity of the catheter shaft and a proximal portion separate from the catheter shaft; placing a distal end of a guidewire through the vascular penetration into the vessel; inserting a proximal end of the guidewire through at least a portion of the guidewire tube; positioning the interventional device through the vascular penetration; and advancing the interventional device through the vessel to position the interventional element at the treatment site, wherein the guidewire is disposed within the guidewire tube between the vascular penetration and the interventional element when the interventional element is at the treatment site. In a preferred aspect, as the interventional device is advanced into the vessel, the guidewire exits the guidewire tube at locations progressively further from the interventional element as the interventional device is inserted. Similarly, when the interventional device is withdrawn, the guidewire exits the guidewire tube at locations progressively closer to the interventional element at the device is withdrawn.

In a further aspect of the method, the guidewire extends out of a slit in a wall of the guidewire tube. The slit may extend from a point no more than about 50 cm proximal to the interventional element to a point at or near the vascular penetration when the interventional element is at the treatment site.

The method may further include positioning a collar in the vascular penetration, the collar being slidably disposed over catheter shaft and the guidewire tube, wherein advancing the interventional device comprises moving the catheter shaft and guidewire tube relative to the collar. The collar may have a wire guide that extends through the slit in the guidewire tube, and wherein moving the guidewire tube relative to the collar guides the guidewire into or out of the guidewire tube. Usually, a hemostasis device is placed in the vascular penetration, and the collar is positioned in the hemostasis device. The hemostasis device provides a hemostatic seal between the hemostasis device and the collar. The interventional device may also include a seal in the collar to inhibit blood leakage from the vessel around the catheter shaft and guidewire tube.

In another aspect of the method, the guidewire tube is collapsible from an extended length to a collapsed length, wherein the guidewire tube has the collapsed length before the interventional device is inserted into the vessel and has the extended length when the interventional element is at the treatment site. The interventional device may include a collar slidable relative to the catheter shaft and coupled to the guidewire tube. In this way, advancing the interventional device relative to the collar extends the length of the guidewire tube.

In preferred embodiments, the interventional element comprises a stent, and the method further comprising deploying the stent at the treatment site. In these embodiments, the interventional element preferably comprises a plurality of stent segments, the method further comprising deploying a first selected number of the stent segments at the treatment site while retaining a second selected number of stent segments on the catheter shaft. The interventional element may also comprise a balloon, wherein the method further comprising expanding the balloon at the treatment site. Preferably, a first selected portion of the balloon is expanded while constraining a second selected portion of the balloon.

In a further aspect of the invention, a method of performing an intervention at a treatment site through a vascular penetration in a vessel comprises providing an interventional device having a catheter shaft, an interventional element coupled to a distal extremity of the catheter shaft, and a guidewire tube having a distal portion coupled to the distal extremity of the catheter shaft; placing a distal end of a guidewire through the vascular penetration into the vessel; positioning a proximal end of the guidewire through at least a portion of the guidewire tube such that the proximal end of the guidewire exits the guidewire tube at a point closer to a distal end of the interventional device than to a proximal end of the interventional device; positioning the interventional device through the vascular penetration; and advancing the interventional device through the vessel to position the interventional element at the treatment site, wherein the guidewire exits the guidewire tube closer to the proximal end of the interventional device than to the distal end of the interventional device when the interventional element is at the treatment site.

Further aspects of the nature and advantages of the invention will become apparent from the following detailed description when taken in conjunction with the drawings.

BRIEF DESCRIPTION OF THE DRAWINGS

FIG. 1 is a side elevational view of a stent delivery catheter according the invention.

FIGS. 2A-2B are side partial cross-sectional views of the stent delivery catheter of FIG. 1 with the balloon deflated and inflated, respectively.

DETAILED DESCRIPTION OF THE INVENTION

Figure 2B:
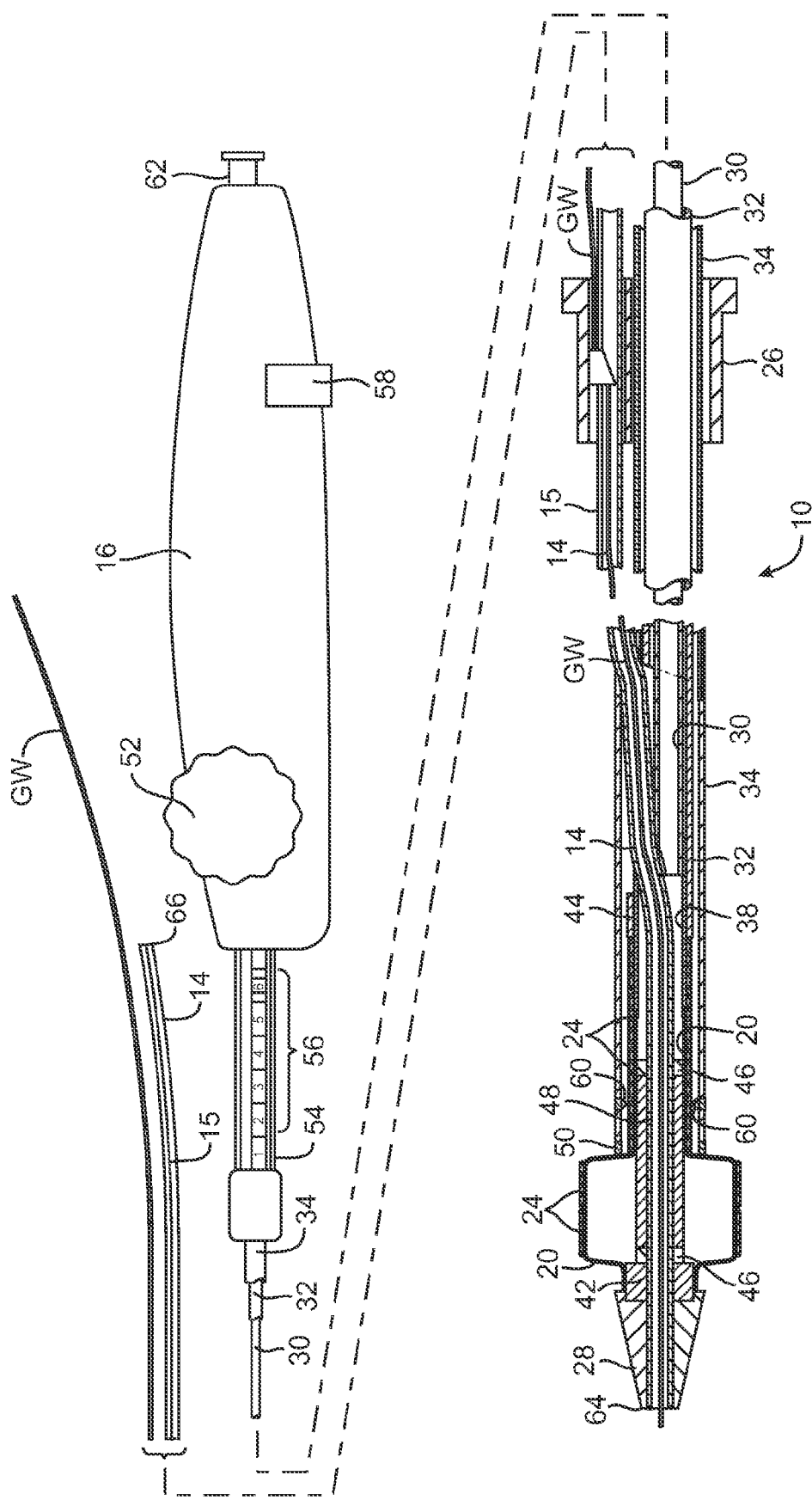

Referring to FIG. 1, a first embodiment of an interventional device according to the invention will be described. In this embodiment, the interventional device is a stent delivery catheter 10 having a catheter body 12, a guidewire tube 14 with a longitudinal slit 15, a handle 16, and an interventional element 18. Interventional element 18 comprises an expandable balloon 20 coupled to catheter body 12, and one or more stents 22 positioned over balloon 20 for expansion therewith. In a preferred embodiment, each stent 22 comprises a plurality of separate or separable stent segments 24, some of which are shown expanded on balloon 20 while others are retained within catheter body 12. Catheter body 12 and guidewire tube 14 extend through a collar 26 and are slidable relative thereto. A guidewire GW extends slidably through guidewire tube 14 between a nosecone 28 at the distal end of catheter body 12 and collar 26.

Delivery catheter 10 has dimensions suitable for use in the anatomical region to be treated. In one embodiment suitable for stent delivery to the coronary arteries, catheter body 12 has a length of about 100-200 cm and an outer diameter of about 0.1-0.5 cm. Balloon 20 may have a length of about 2-12 cm and an expanded diameter of about 2-10 mm. Balloon 20 may also be tapered, stepped, or have other geometry suitable for the target region. Stent segments are preferably about 2-10 mm in length and have an unexpanded diameter of about 0.5-2 mm. Guidewire tube 14 has an outer diameter of about 0.3-0.6 mm, an inner diameter of about 0.2-0.5 mm, and a length approximately the same as that of catheter body 12.

Catheter body 12 includes, as further illustrated in FIGS. 2A-2B, a tubular inflation shaft 30, a tubular pusher 32 slidably disposed over inflation shaft 30, and a tubular sheath 34 slidably disposed over pusher 32. Guidewire tube 14 extends slidably through a port 36 in sheath 34 and passes through balloon 20 and nosecone 28, to which it is attached. Balloon 20 has a proximal balloon leg 38 fixed at its proximal end to guidewire tube 14 and inflation shaft 30, and at its distal end to a stent stop 42 fixed to guidewire tube 14 and/or nosecone 28. Stent segments 24 are slidably disposed over balloon leg 38 and balloon 20. An endring 44 attached to pusher 32 engages the proximal-most stent segment 24P and facilitates advancing the line of stent segments 24 distally relative to balloon 20. A plurality of radiopaque markers 46 are fixed to guidewire tube 14 within balloon 20 to facilitate positioning of catheter 20 using fluoroscopy. A build-up 48 is optionally provided around guidewire tube 14 within balloon 20 to enhance frictional engagement between balloon 20 and stent segments 24 when the balloon is deflated. Sheath 34 has a metallic reinforcing ring 50 at its distal end that resists expansion when balloon 20 is inflated. Other aspects of the construction and operation of delivery catheter 10 are described in copending application Ser. No. 10/637,713, filed Aug. 8, 2003, which is incorporated herein by reference.

When stent segments 24 are to be deployed, sheath 34 is retracted relative to balloon 20 as illustrated in FIG. 2B. A knob 52 on handle 16 is coupled to a sheath housing 54 which is attached to sheath 34, whereby knob 52 is rotated to retract sheath 34. Indicia 56 are provided on sheath housing 54 to indicate the distance that the sheath has been retracted and/or the number of stent segments 24 exposed on balloon 20 distally of sheath 24. Other aspects of handle 16 are described in copending application Ser. No. 10/746,466, filed Dec. 23, 2003, entitled "Devices and Methods for Controlling and Indicating the Length of an Interventional Element," which is incorporated herein by reference.

As sheath 34 is retracted, pusher 32 may be either in a locked or unlocked mode. A pivotable switch 58 on handle 16 is coupled to pusher 32 and is movable between a first position in which pusher 32 is decoupled from sheath 34 and held in a fixed position relative to balloon 20 (locked), and a second position in which pusher 32 is coupled so as to move with sheath 34 (unlocked). In the locked mode, pusher 32 exerts force distally against stent segments 24 as sheath 34 is retracted, maintaining their position on balloon 20. This allows the user to expose the desired number of stent segments 24 that are to be deployed according to the length of the lesion being treated. In the unlocked mode, pusher 32 is allowed to move proximally relative to balloon 20 as sheath 34 is retracted. An annular ridge 60 on the inner wall of sheath 34 near its distal end is configured to engage stent segments 24 whereby, in the absence of force exerted by pusher 32, stent segments 24 slide proximally with sheath 34 as the sheath is retracted. This may be used for two purposes: First, it allows the user to expose a desired length of balloon 20 without any of stent segments 24 thereon to perform pre- or post-dilatation at the treatment site. Second, it allows the user to create a small gap separating the exposed stent segments 24 to be deployed from those retained within sheath 34 so that upon balloon expansion, the segments 24 remaining in sheath 34 are not expanded or deformed.

When the desired length of balloon 20 and/or number of stent segments 24 have been exposed distally of sheath 34, balloon 20 may be expanded by delivering an inflation fluid through inflation port 62 on handle 16. Inflation port 62 communicates with inflation shaft 30 to deliver the inflation fluid to the interior of balloon 20. Stent segments 24 are preferably a malleable metal such as stainless steel, cobalt chromium, MP35N or other suitable material that plastically deforms as balloon 20 is inflated to maintain stent segments 24 in an expanded tubular configuration. Self-expanding stent materials including shape memory or superelastic alloys such as Nitinol as well as various polymers may also be utilized. Biodegradable polymer stents, stent-grafts, covered stents, and various other stent-like structures may also be deployed using catheter 20. Any of these various types of stents may be impregnated, coated, or otherwise combined with polymers, ceramics, metals, proteins, and/or therapeutic agents to enhance their effectiveness and/or to reduce restenosis. In a preferred embodiment, stent segments 24 are coated first with a polymeric undercoat or primer such as parylene then with a biodegradable polymeric coating comprising a poly-lactic-acid mixed or combined with an anti-restenosis agent such as taxol, rapamycin, or analog of either. Other aspects of stent segments 24 are described in copending application Ser. No. 10/738,666, filed Dec. 16, 2003, entitled "Multiple Independent Nested Stent Structures and Methods for Their Preparation and Deployment," which is incorporated herein by reference.

Longitudinal slit 15 in guidewire tube 14 extends from the proximal end 66 of guidewire tube 14 to a point in the distal half of catheter 20, preferably near balloon 20. While slit 15 could extend through balloon 20 all the way to the distal tip of guidewire tube 14, in a preferred embodiment, slit 15 terminates at a point about 20-50 cm proximally of the distal tip 64 of nosecone 28, and about 10-40 cm proximally of the proximal end of the expandable portion of balloon 20. The distal end of slit 15 may be disposed either within or outside of sheath 34, but is preferably outside of sheath 34, e.g. about 0.1-10 cm proximal to port 36 when sheath 34 is in a fully distal position. Slit 15 preferably extends all the way to the proximal end 66 of guidewire tube 14, although slit 15 may alternatively terminate some distance distally of proximal end 66, but preferably no more than about 30 cm therefrom and usually no more than one-half the distance to the distal tip 64 from proximal end 66.

Figure 3A:
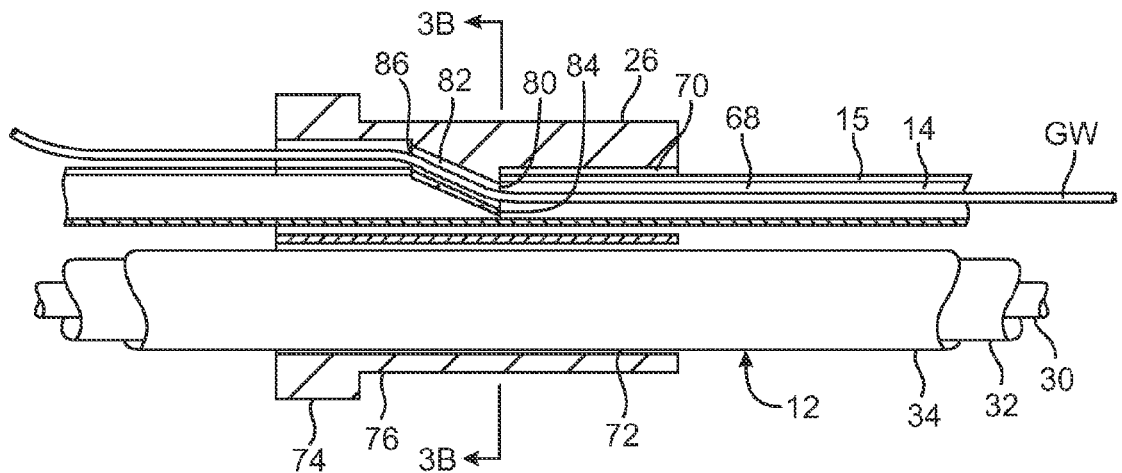
FIG. 3A is a side cross-sectional view of a collar in the stent delivery catheter of FIG. 1.
Figure 3B:
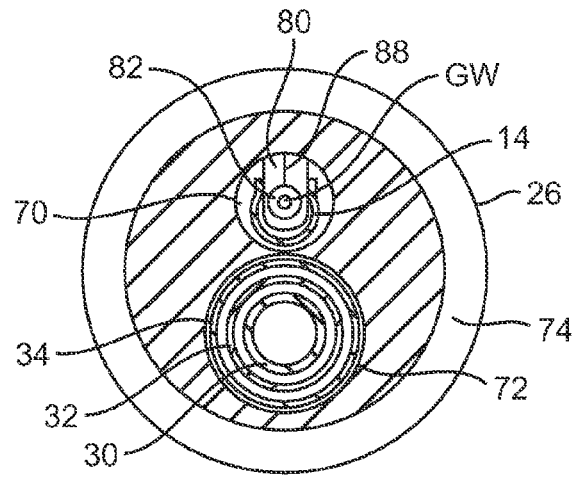
FIG. 3B is a transverse cross-section of the collar of FIG. 3A.
Figure 3C:
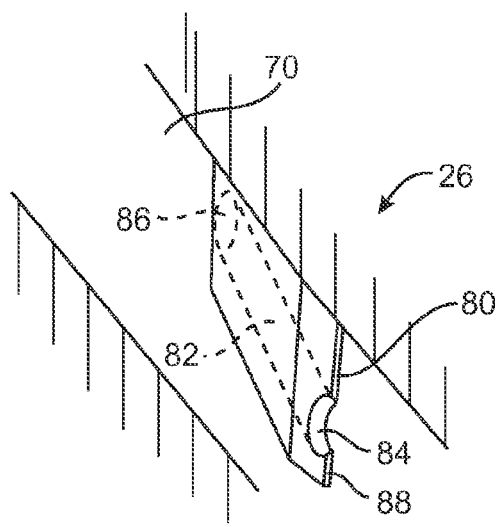
FIG. 3C is an oblique partial cross sectional view of the collar of FIG. 3A.

As illustrated in FIGS. 3A-3C, collar 26 has a first channel 70 configured to receive guidewire tube 14 and a second channel 72 configured to receive catheter body 12. Preferably, first and second channels 70, 72 are configured to provide a slidable, sealed fit with guidewire tube 14 and catheter body 12 so as to minimize blood leakage therethrough. Optionally, elastomeric seals or valves (not shown) may be provided in one or both of channels 70, 72 to seal against the exterior of guidewire tube 14 and catheter body 12 to further inhibit blood leakage. Collar 26 is configured to be inserted through a rotating hemostasis valve (RHV) of a guiding catheter or other hemostatic device placed in a vascular penetration. A flange 74 is disposed around the proximal end of collar 26 to seat against the RHV and prevent over-insertion. The exterior surface 76 of collar 26 is configured to seal within the RHV to inhibit leakage of blood around collar 26.

A wedge-shaped wire guide 80 extends radially inwardly into first channel 70 and is configured to extend through slit 15 into guidewire tube 14. Wire guide 80 has a passage 82 through which guidewire GW may slide. Passage 82 is disposed at an oblique angle relative to the axial direction such that the distal opening 84 in passage 82 is aligned with guidewire lumen 68, while the proximal opening 86 is radially offset from guidewire lumen 68, outside of guidewire tube 14. In this way, as guidewire tube 14 moves distally relative to collar 26, guidewire GW is guided into guidewire tube 14, while moving guidewire tube proximally relative to collar 26 removes guidewire GW from guidewire tube 14.

Thus, guidewire GW is disposed within guidewire tube 14 between collar 26 and distal end 64 of catheter 10, but is outside of guidewire tube 14 between collar 26 and proximal end 66 of guidewire tube 14 (or handle 16). To facilitate sliding movement of wire guide 80 through slit 15, wire guide 80 has a tapered, beveled, or rounded leading edge 88 that helps to engage and widen slit 15.

Figure 4A:
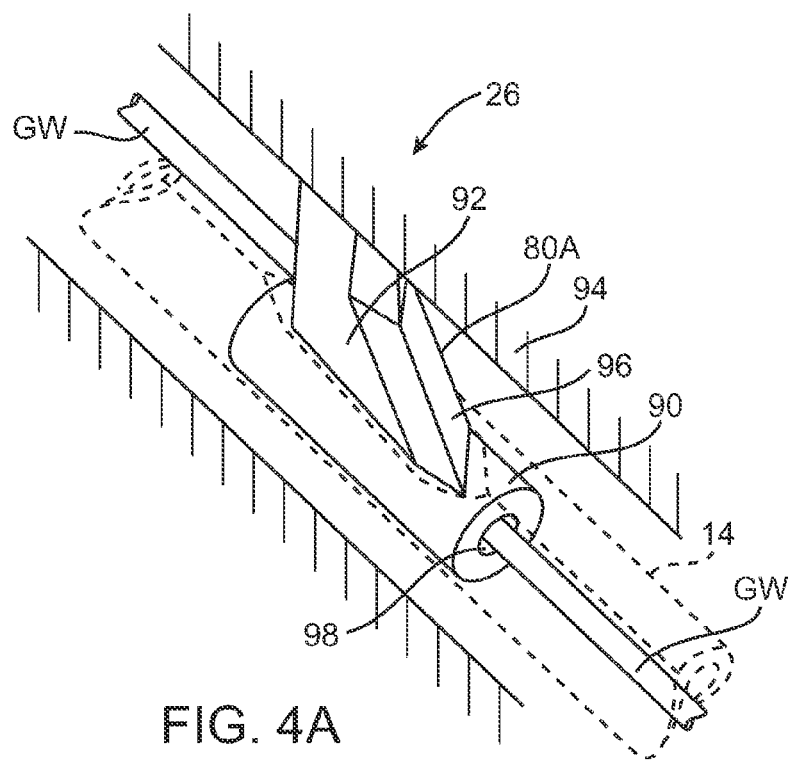
FIG. 4A is an oblique partial cross sectional view of a further embodiment of a collar in a stent delivery catheter according to the invention.
Figure 4B:
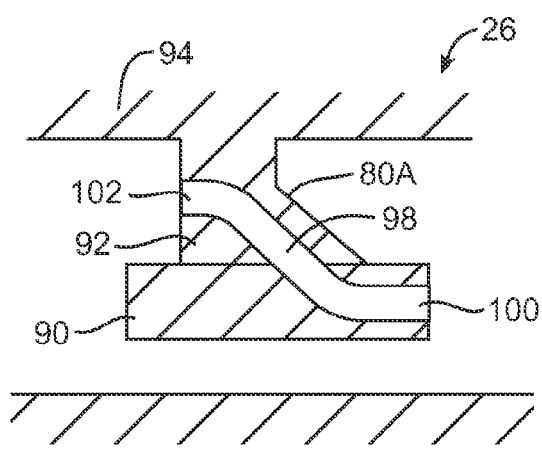
FIG. 4B is a partial side cross sectional view of a wire guide in the collar of FIG. 4A.
Figure 4C:
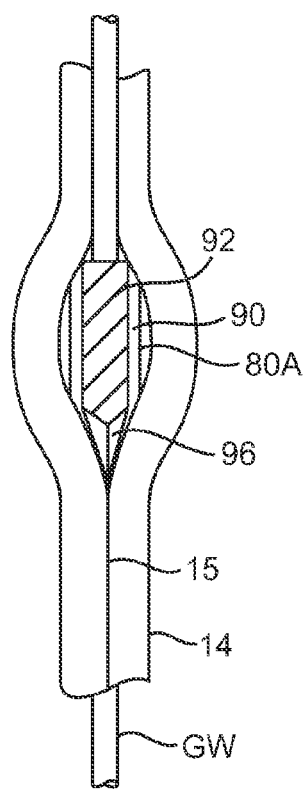
FIG. 4C is a partial top cross sectional view of a wire guide in the collar of FIG. 4A.

A second embodiment of a wire guide 80A in collar 26 is illustrated in FIGS. 4A-4C. Wire guide 80A includes a generally cylindrical bottom tube 90 configured to slide within guidewire lumen 68. Bottom tube 90 may be round, oval, elliptical, disk-shaped or other suitable shape in cross-section, and may have a pointed, conical, bullet-shaped, or rounded leading edge to assist in tracking through guidewire lumen 68. Bottom tube 90 is fixed to a base 92 attached to the wall 94 of collar 26. Base 92 is configured to extend through slit 15 in guidewire tube 14. The leading edge 96 of base 92 may be tapered, peaked, rounded or have other suitable shape to assist in sliding through and spreading slit 15. A passage 98 extends from a distal opening 100 in bottom tube 90 to a proximal opening 102 on the proximal side of base 92. Distal opening is aligned with guidewire lumen 68, while proximal opening 102 is radially offset therefrom so that guidewire GW is guided from being within guidewire lumen 68 distally of wire guide 80A to being outside guidewire lumen 68 proximally of wire guide 80A.

Figure 5A:
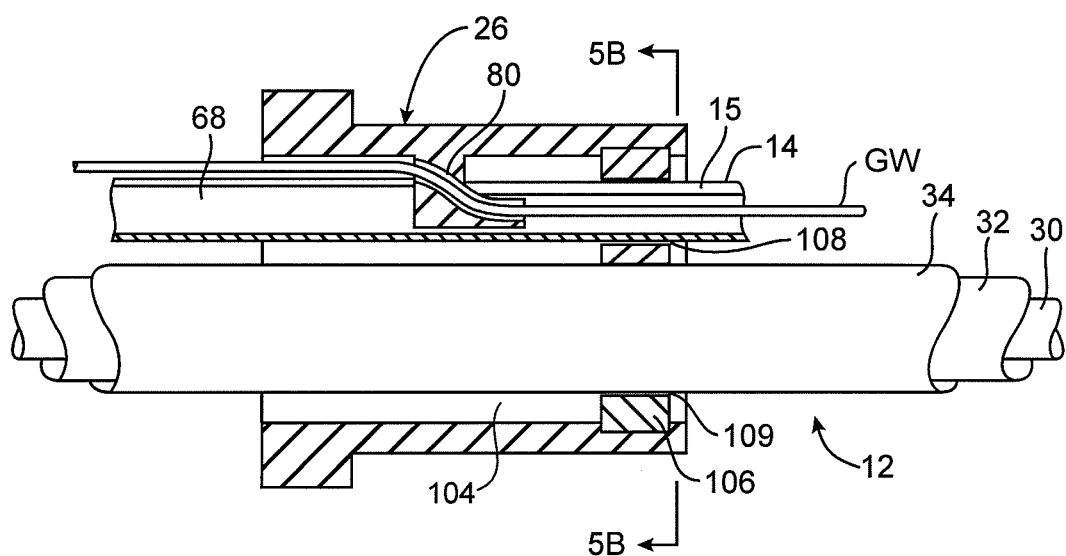
FIG. 5A is a side cross-section of another embodiment of a collar in an interventional catheter according to the invention.
Figure 5B:
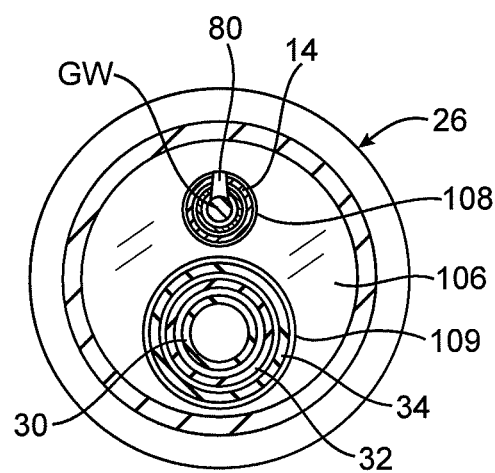
FIG. 5B is a transverse cross-section of the collar of FIG. 5A.

A further embodiment of collar 26 is illustrated in FIGS. 5A-5B. In this embodiment, collar 26 has a single channel 104 extending axially therethrough. Channel 104 is configured to receive both guidewire tube 14 and catheter body 12. A wire guide 80, which may have any of the configurations described above, extends into channel 104 from the wall of collar 26. Wire guide 80 is configured to extend through slit 15 in guidewire tube 14 and guides guidewire GW into and out of guidewire lumen 68 as guidewire tube 14 is moved distally or proximally relative to collar 26. In order to minimize leakage of blood through channel 104, an elastomeric hemostatic seal 106 is mounted within collar 26 across channel 104. Seal 106 has a first hole 108 configured to slidably receive and seal against the exterior of guidewire tube 14, and a second hole 109 configured to slidably receive and seal against the exterior of catheter body 12. Seal 106 may be of various elastomeric materials and may have any suitable design to provide hemostatic sealing, including diaphragm, duckbill, slit, flapper, or other type.

Figure 6:
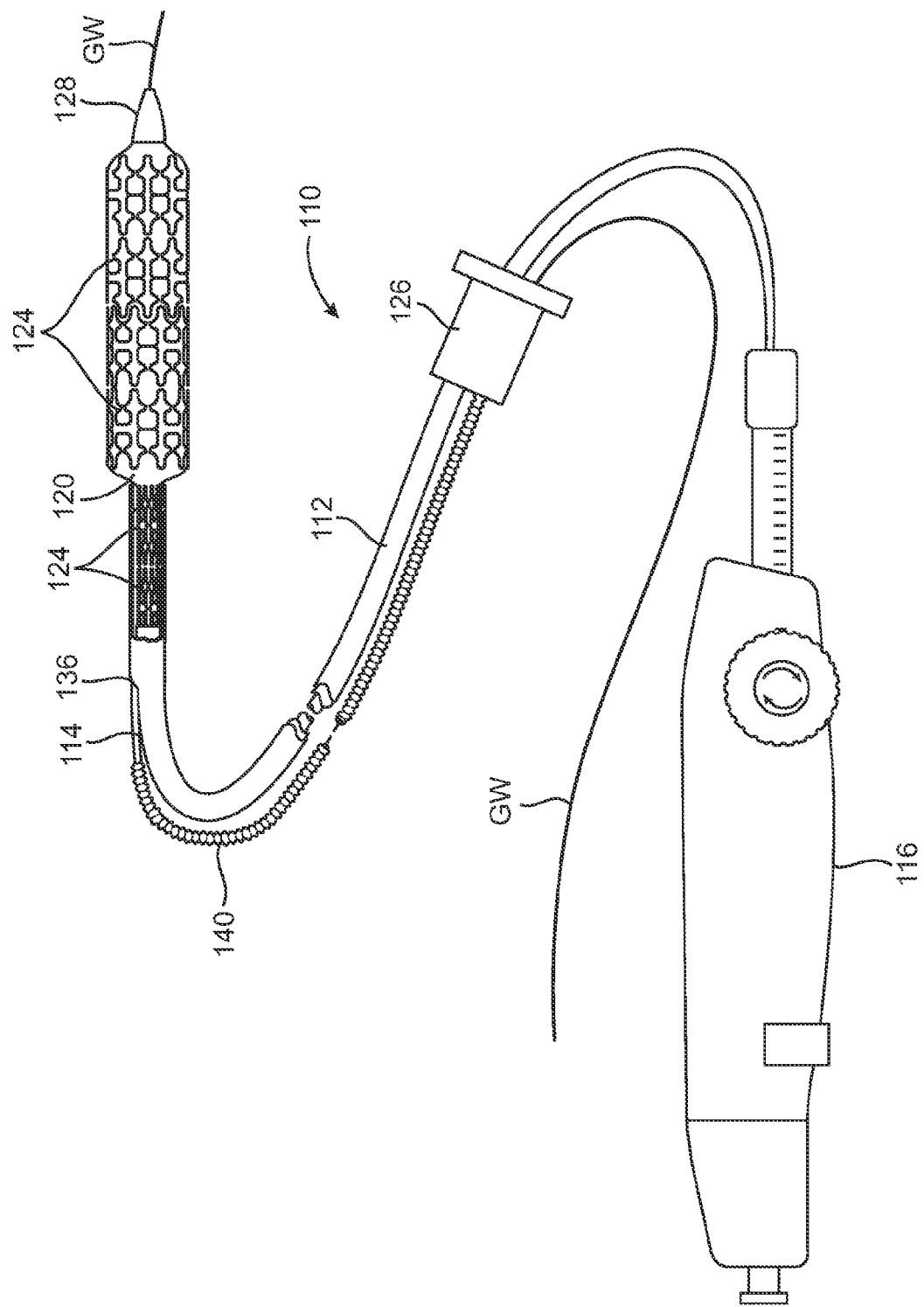
FIG. 6 is a side elevational view of a stent delivery catheter according to the invention in a further embodiment thereof.

Another embodiment of an interventional device according to the invention is illustrated in FIG. 6. In this embodiment, delivery catheter 110 has a catheter body 112, handle 116, balloon 120, stent segments 124, and nosecone 128 constructed as described above in connection with FIGS. 1-2. Guidewire tube 114 extends from nosecone 128 through balloon 120 and out of a port 136 in catheter body 112 as described above. A collar 126 is slidably disposed around guidewire tube 114 and catheter body 112 and is configured to be placed in a vascular penetration or in a hemostasis valve of a guide catheter or other access device.

Unlike previous embodiments, guidewire tube 114 is collapsible from an extended length approximately the same as that of catheter body 112, to a substantially shorter collapsed length, e.g. 5-50 cm, more preferably 10-30 cm. These lengths will of course vary according to the region in which the interventional catheter is to be used, but generally the collapsed length will be less than about 50%, usually about 10%-40%, and preferably less than about 30% of the extended length. In an exemplary configuration, guidewire tube 114 has a collapsible section 140 extending from a point near port 136 proximally to collar 126, to which it is attached. In this way, as catheter body 112 is moved distally relative to collar 126, guidewire tube 114 is extended, while as catheter body 112 is moved proximally relative to collar 126, guidewire tube 114 is collapsed. This effectively makes the point at which guidewire GW exits the guidewire tube movable relative to catheter body 112 from a location near balloon 120 to a location near handle 116 depending upon the distance catheter 110 has been inserted into the vessel. At the same time, from collar 126 all the way to the tip of nosecone 128, guidewire GW is entirely enclosed within guidewire tube 114 regardless of how far catheter 110 has been introduced.

Figure 7A:
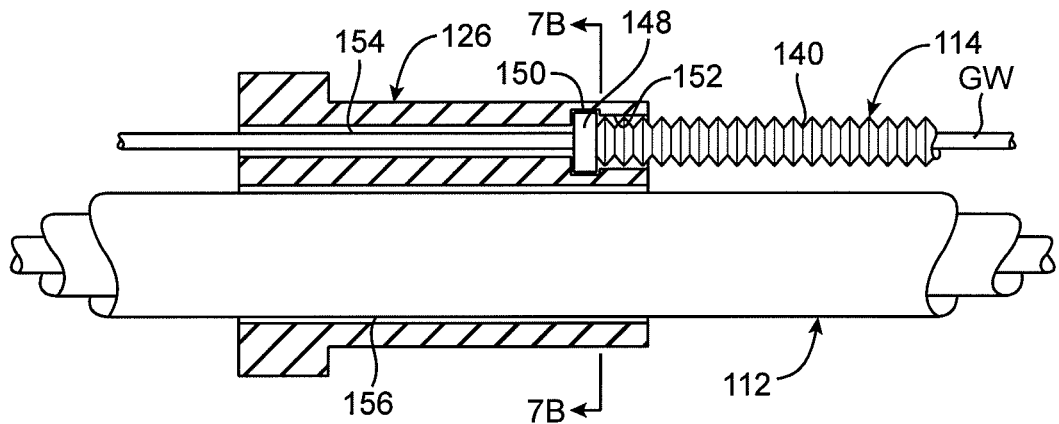
FIG. 7A is a side cross-section of a collar in the stent delivery catheter of FIG. 6.
Figure 7B:
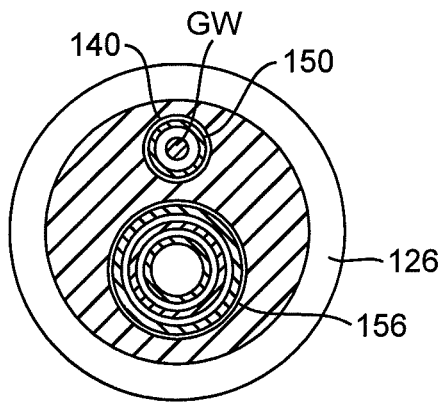
FIG. 7B is a transverse cross-section of the collar of FIG. 7A.
Figure 7C:
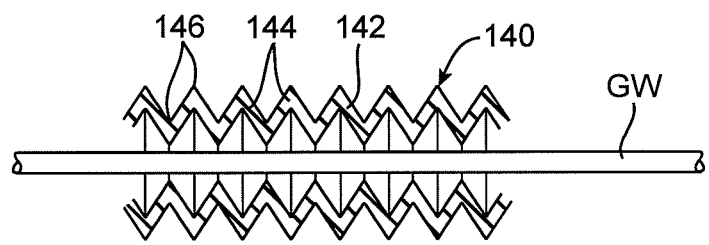
FIG. 7C is a side cross-section of a guidewire tube in the stent delivery catheter of FIG. 6.

Collapsible guidewire tube 114 may have various constructions. In an exemplary embodiment, illustrated in FIGS. 7A-7C, the collapsible portion 140 of guidewire tube 114 has an accordion-like structure, with walls 142 having a zig-zag cross-section. Collapsible portion 140 comprises a series of conical or dome shaped segments 144 interconnected by hinges 146 that allow the segments to pivot toward and away from each other as guidewire tube 114 is collapsed or extended. In some embodiments, the conical or dome-shaped segments may be configured to nest within one another in the collapsed configuration. Optionally, an additional support tube (not illustrated) may be disposed within guidewire tube 114 extending from its proximal end distally through a portion of the guidewire tube, e.g. 10-30 cm, to keep the guidewire lumen open so that guidewire GW slides smoothly as guidewire tube 114 is collapsed.

At its proximal end, guidewire tube 114 has a flange 148 of larger diameter that is disposed within a cylindrical chamber 150 in collar 126. A shoulder 152 retains flange 148 within chamber 150. Preferably, flange 148 fits snugly within chamber 150 to provide a hemostatic seal. A first channel 154 through collar 126 is aligned with chamber 150 and permits the passage of guidewire GW through the collar. A second channel 156 is configured to slidably receive catheter body 112, preferably with a fit tight enough to resist leakage of blood. Optionally, an elastomeric hemostatic seal may be provided in either or both of channels 154, 156.

The methods of using the interventional devices of the invention will now be described. While the methods will be described in the context of delivering stents into the coronary arteries, it should be understood that the invention will have utility in performing various diagnostic and treatment procedures in other regions including in peripheral arteries such as the femoral, iliac, and carotid arteries, veins and vein grafts, blood vessels of the brain, organs such as the heart, liver, and kidneys, biliary vessels, intestinal and urinary vessels and organs, lungs, genital organs, and other regions. In addition to stent delivery catheters, the principles of the invention may be applied to various other types of devices including those for angioplasty, drug delivery, delivery of embolic devices, repair of aneurysms, RF mapping and ablation, treatment of atrial fibrillation, heart valve repair and replacement, vascular occlusion, valvuloplasty, intravascular ultrasound, endoscopic visualization, delivery of implantable devices, defect repair, and other purposes.

Referring to the embodiment of FIG. 1, a vascular access site is first selected in a peripheral vessel such as a femoral artery. An introducer is first placed into the vessel through a puncture, incision or other penetration and a first, larger guidewire is placed through the introducer into the aorta. A guiding catheter is then placed through the introducer over the guidewire, advanced over the aortic arch and into the ostium of the left or right coronary artery. The first guidewire is withdrawn. The guiding catheter will have a rotating hemostasis valve (RHV) on its proximal end that facilitates the introduction of devices while maintaining a seal against the leakage of blood from the vessel. A second smaller guidewire GW is next inserted into the vessel through the RHV, advanced through the guiding catheter into the target coronary artery, and positioned across the stenotic lesion to be treated. The proximal end of guidewire GW is threaded through the guidewire tube 14 on delivery catheter 10. Delivery catheter 10 is advanced over the guidewire into the guiding catheter and collar 26 is inserted into the RHV, which is then tightened to clamp collar 26 in place and seal around its periphery. On the proximal side of collar 26, guidewire GW is disposed outside of guidewire lumen 14 and available for the physician to hold as delivery catheter 10 is advanced over the guidewire into the target vessel. As delivery catheter 10 is advanced distally relative to collar 26, wire guide 80 automatically inserts guidewire GW into guidewire tube 14 through slit 15 so that inside the vessel, guidewire GW is fully enclosed within guidewire tube 14.

Delivery catheter 10 is positioned under fluoroscopic visualization such that the distal end of balloon 20 is even with or just beyond the distal end of the target lesion. Sheath 34 is retracted relative to balloon 20, exposing a desired portion of balloon 20. Initially, pusher 32 may be in "unlocked" mode wherein it moves proximally with sheath 34, allowing stent segments 24 to slide off of the exposed portion of balloon 20. Balloon 20 is then inflated to predilate the lesion. Balloon 20 is then deflated and retracted into sheath 34, and the device is repositioned within the target lesion. Sheath 34 is again retracted, this time with pusher 32 in "locked" mode so as to maintain stent segments 24 in position on balloon 20. Sheath 34 is retracted to expose the desired number of stents corresponding to the length of the lesion being treated. Balloon 20 is inflated to expand stent segments 24 into engagement with the vessel wall. The device may then be repositioned at a different lesion, and the process repeated.

When delivery catheter 10 is withdrawn from the vessel, because wire guide 80 automatically removes guidewire GW from guidewire tube 14, the guidewire is continuously exposed outside the catheter and available for the physician to manipulate at close proximity to the vascular penetration. Advantageously, if delivery catheter 10 is to be exchanged with another catheter, the physician can remove the first catheter from the guidewire and replace it with a second catheter without having to move away from the patient or rely upon the help of an assistant to hold the proximal end of the guidewire.

From the operator's point of view, the embodiment of FIGS. 6-7 works much the same as that of FIG. 1. Delivery catheter 110 is introduced and operated as just described, the primary difference being that guidewire tube 114 is initially in a collapsed configuration outside the body when guidewire GW is first inserted through it. Guidewire lumen 114 then automatically extends from a collapsed length to an extended length as delivery catheter 110 is advanced to the treatment site. When catheter 110 is withdrawn from the vessel, guidewire tube 114 automatically collapses to a shorter length. Again, outside the body, guidewire GW always remains exposed outside the catheter and available for manipulation by the physician proximal to collar 26.

While the above is a complete description of the preferred embodiments of the invention, various alternatives, modifications, substitutions, equivalents, and additions are possible without departing from the scope thereof, which is defined by the claims.

What is claimed is:

1. A method of performing an intervention at a treatment site through a vascular penetration in a vessel, the method comprising:

providing an interventional device comprising:

a catheter shaft; an interventional element coupled to a distal extremity of the catheter shaft; and a guidewire tube having a distal portion coupled to the distal extremity of the catheter shaft and a proximal portion separate from the catheter shaft;

a collar forming first and second longitudinal passageways, each passageway forming a lumen;

placing a distal end of a guidewire through the vascular penetration into the vessel;

inserting the catheter shaft through the first longitudinal passageway of the collar;

inserting the guidewire tube through the second longitudinal passageway of the collar, the lumen of the second longitudinal passageway being unconnected and discrete from the lumen of the first longitudinal passageway;

inserting the guidewire through at least a portion of the guidewire tube, wherein a proximal end of the guidewire extends out of a slit in a wall of the guidewire tube;

positioning the interventional device through the vascular penetration;

positioning the collar adjacent the vascular penetration, the collar being slidably disposed over the catheter shaft and the guidewire tube; and advancing the interventional device through the vessel to position the interventional element at the treatment site by distally advancing the catheter shaft and guidewire tube relative to the collar;

wherein the collar comprises a wire guide that extends through the slit in the guidewire tube, and wherein distally advancing the guidewire tube relative to the collar guides the guidewire through the wire guide into the guidewire tube.

2. The method of claim 1 wherein the slit extends from a point no more than 50 cm proximal to the interventional element to a point proximal to the vascular penetration when the interventional element is at the treatment site.

3. The method of claim 1 further comprising positioning a hemostasis device in the vascular penetration, the collar being positioned in the hemostasis device.

4. The method of claim 3 further comprising providing a hemostatic seal between the hemostasis device and the collar.

5. The method of claim 1 further comprising providing a seal in the collar to inhibit blood leakage from the vessel around the catheter shaft or guidewire tube.

6. The method of claim 1 wherein the interventional element comprises a stent, the method further comprising deploying the stent at the treatment site.

7. The method of claim 1 wherein the interventional element comprises a plurality of stent segments, the method further comprising deploying a first selected number of the stent segments at the treatment site while retaining a second selected number of stent segments on the catheter shaft.

8. The method of claim 1 wherein the interventional element comprises a balloon, the method further comprising expanding the balloon at the treatment site.

9. The method of claim 8 further comprising expanding a first selected portion of the balloon while constraining a second selected portion of the balloon.

10. The method of claim 1 further comprising withdrawing the interventional device from the vessel, wherein the guidewire exits the guidewire tube at locations progressively closer to the interventional element as the interventional device is withdrawn.

11. A method of performing an intervention at a treatment site through a vascular penetration in a vessel, the method comprising:

providing an interventional device comprising:
  a catheter shaft having an inflation tube disposed therein;
  an interventional element coupled to a distal extremity of the catheter shaft, the interventional element comprising a balloon that is expandable via the inflation tube; and
  a guidewire tube having a distal portion coupled to the distal extremity of the catheter shaft;
  a collar forming first and second longitudinal passageways, each passageway forming a lumen;
placing a distal end of a guidewire through the vascular penetration into the vessel;
inserting the catheter shaft through the first longitudinal passageway of the collar;
inserting the guidewire tube through the second longitudinal passageway of the collar, the lumen of the second longitudinal passageway being unconnected and discrete from the lumen of the first longitudinal passageway;
positioning the guidewire through at least a portion of the guidewire tube such that a proximal end of the guidewire exits the guidewire tube through a slit in a wall of the guidewire tube;
positioning the interventional device through the vascular penetration;
positioning the collar adjacent the vascular penetration, the collar being slidably disposed over the catheter shaft and the guidewire tube; and
advancing the interventional device through the vessel to position the interventional element at the treatment site by distally advancing the catheter shaft and guidewire tube relative to the collar;
  wherein the collar comprises a wire guide that extends through the slit in the guidewire tube, and wherein distally advancing the guidewire tube relative to the collar guides the guidewire through the wire guide into the guidewire tube.

12. The method of claim 11, wherein the spacing between an axis of the first longitudinal passageway and an axis of the second longitudinal passageway is greater in a proximal portion of the collar than in a distal portion of the collar.

13. The method of claim 11, wherein the guidewire and the guidewire tube extend through a first portion of the first longitudinal passageway with the guidewire disposed within the guidewire tube, and wherein the guidewire and the guidewire tube extend through a second portion of the first longitudinal passageway with the guidewire disposed outside the guidewire tube.

* * * * *